(12) United States Patent
Buckner et al.

(10) Patent No.: US 8,053,235 B2
(45) Date of Patent: Nov. 8, 2011

(54) METHODS OF GENERATING ANTIGEN-SPECIFIC CD4+CD25+REGULATORY T CELLS, COMPOSITIONS AND METHODS OF USE

(75) Inventors: Jane H. Buckner, Seattle, WA (US); Mindi R. Walker, Coatesville, PA (US)

(73) Assignee: Benaroya Research Institute at Virginia Mason, Seattle, WA (US)

(*) Notice: Subject to any disclaimer, the term of this patent is extended or adjusted under 35 U.S.C. 154(b) by 362 days.

(21) Appl. No.: 11/261,429

(22) Filed: Oct. 28, 2005

(65) Prior Publication Data
US 2006/0115899 A1 Jun. 1, 2006

Related U.S. Application Data

(60) Provisional application No. 60/623,380, filed on Oct. 29, 2004.

(51) Int. Cl.
*A01N 1/02* (2006.01)
*C12N 5/071* (2010.01)

(52) U.S. Cl. .................................. 435/372.3; 435/2

(58) Field of Classification Search .................. None
See application file for complete search history.

(56) References Cited

U.S. PATENT DOCUMENTS

| 6,316,257 | B1 | 11/2001 | Flyer et al. |
| 6,576,428 | B1* | 6/2003 | Assenmacher et al. ........ 435/7.1 |
| 6,667,175 | B1 | 12/2003 | Suciu-Foca |
| 6,759,239 | B2 | 7/2004 | Suciu-Foca et al. |
| 2003/0073102 | A1 | 4/2003 | Kwok et al. |
| 2003/0157057 | A1 | 8/2003 | Horwitz |
| 2004/0175373 | A1 | 9/2004 | Berenson et al. |
| 2004/0185034 | A1 | 9/2004 | Horwitz |
| 2004/0191235 | A1 | 9/2004 | Groux et al. |
| 2005/0186207 | A1 | 8/2005 | Bluestone et al. |
| 2005/0196386 | A1 | 9/2005 | Blazar et al. |

FOREIGN PATENT DOCUMENTS

| WO | WO 03/059264 A3 | 7/2003 |
| WO | WO 2004/060145 A2 | 7/2004 |

OTHER PUBLICATIONS

Horwitz et al., 2004, Seminars in Immunology, vol. 16: 135-143.*
Von Herrath et al., 2003, Nat. Reviews, vol. 3: 223-232.*
Fantini et al., May 2004, J. Immunol. vol. 172: 5149-5153.*
Chen, C., et al., "Induction of Autoantigen-Specific Th2 and Tr1 Regulatory T Cells and Modulation of Autoimmune Diabetes," Journal of Immunology 171:733-744, 2003.
Chen, W., et al., "Conversion of Peripheral CD4+CD25− Naive T Cells to CD4+CD25+ Regulatory T Cells by TGF-β Induction of Transcription Factor Foxp3," Journal of Experimental Medicine 198(12):1875-1886, 2003.
Zheng, S.G., et al., "Generation Ex Vivo of TGF-β-Producing Regulatory T Cells From CD4+CD25− Precursors," Journal of Immunology 169:4183-4189, 2002.
Baecher-Allan, C., et al., "CD4+CD25$^{high}$ Regulatory Cells in Human Peripheral Blood," Journal of Immunology 167:1245-1253, 2001.
Bill, J.R., and B.L. Kotzin, "Use of Soluble MHC Class II/Peptide Multimers to Detect Antigen-Specific T Cells in Human Disease," Arthritis Research 4(4):261-265, 2002.
Bluestone, J.A., and Q. Tang, "Therapeutic Vaccination Using CD4+CD25+Antigen-Specific Regulatory T Cells," PNAS Early Edition, 2004.
Buckner, J.H., et al., "Defining Antigen-Specific Responses With Human MHC Class II Tetramers," J. Allergy Clin. Immunol. 110(2): 199-208, Aug. 2002.
Cao, D., et al., "CD25$^{bright}$ CD4+Regulatory T Cells Are Enriched in Inflamed Joints of Patients With Chronic Rheumatic Disease," Arthritis Research & Therapy 6(4):R335-R346, Jun. 7, 2004.
Cleland, L.G., and G. Mayrhofer, "Mucosal Tolerance and Rheumatoid Arthritis," British Journal of Rheumatology 36(11):1139-1143, 1997.
Ettinger, R.A., and G.T. Nepom, "Molecular Aspects of HLA Class II αβ Heterodimers Associated With IDDM Susceptibility and Protection," Rev. Immunogenetics 2:88-94, 2000.
Joffre, O., et al., "Induction of Antigen-Specific Tolerance to Bone Marrow Allografts With CD4+CD25+ T Lymphocytes," Blood 103(11):4216-4221, Jun. 1, 2004.
Mallet-Designe, V.I., et al., "Detection of Low-Avidity CD4+ T Cells Using Recombinant Artificial APC: Following the Antiovalbumin Immune Response," J. Immunol. 170:123-131, 2003.
Nakamura, K., et al., "Cell Contact-Dependent Immunosuppression by CD4+ CD25+ Regulatory T Cells is Mediated by Cell Surface-Bound Transforming Growth Factor β," Journal of Experimental Medicine 194(5):629-644, Sep. 3, 2001. Nepom, G.T., et al., "HLA Class II Tetramers: Tools for Direct Analysis of Antigen-Specific CD4+ T Cells," Arthritis & Rheumatism 46(1):5-12, Jan. 2002.
Nepom, G.T., et al., "MHC Peptide Tetramer Core," Immune Tolerance Network, 2002-2003, <http://www.immunetolerance.org/research/core/facilities/mhcpeptide.html> [retrieved Oct. 6, 2004].
Novak, E.J., et al., "MHC Class II Tetramers Identify Peptide-Specific Human CD4+ T Cells Proliferating in Response to Influenza A Antigen," Journal of Clinical Investigation 104:R63-R67, 1999.
Reijonen, H., et al., "Detection of GAD65-Specific T-Cells by Major Histocompatibility Complex Class II Tetramers in Type 1 Diabetic Patients and At-Risk Subjects," Diabetes 51:1375-1382, May 2002.
Sakaguchi, S., et al., "Immunologic Self-Tolerance Maintained by Activated T Cells Expressing IL-2 Receptor α-Chains (CD25)," Journal of Immunology 155:1151-1164, 1995.
Schubert, L.A., et al., "Scurfin (FOXP3) Acts As a repressor of Transcription and Regulates T Cell Activation," Journal of Biological Chemistry 276(40):37672-37679, Oct. 5, 2001.

(Continued)

Primary Examiner — Amy Juedes
(74) Attorney, Agent, or Firm — Christensen O'Connor Johnson Kindness PLLC

(57) ABSTRACT

The present invention provides methods for generating mammalian T cell populations comprising antigen-specific CD4+CD25+ regulatory T cells from freshly isolated CD4+CD25− T cells. The method comprises selecting CD4+CD25− T cells from a sample obtained from a mammalian subject; determining the MHC Class II type of the subject; inducing the generation of antigen-specific regulatory T cells by contacting the isolated CD4+CD25− T cells in a culture vessel with an induction agent for a time period sufficient to generate antigen-specific CD4+CD25+ regulatory T cells; and selecting the CD4+CD25+ antigen-specific regulatory T cells by sorting the cells in the induction culture with a selection agent comprising at least one artificial multimeric MHC Class II/peptide complex that corresponds to the MHC Class II type of the subject.

19 Claims, 23 Drawing Sheets

OTHER PUBLICATIONS

Taams, L.S., et al., "Antigen-Specific T Cell Suppression by Human CD4+CD25+ Regulatory T Cells," *Eur. J. Immunol.* 32:1621-1630, 2002.

Takahashi, K., et al., "Origins and Divergence Times of Mammalian Classs II MHC Gene Clusters," *Journal of Heredity* 91(3):198-204, 2000.

Tang, Q., et al., "*In Vitro*-Expanded Antigen-Specific Regulatory T Cells Suppress Autoimmune Diabetes," *J. Exp. Med.* 199(11):1455-1465, Jun. 7, 2004.

Vigouroux, S., et al., "Antigen-Induced Regulatory T Cells," *Blood* 104(1):26-33, Jul. 1, 2004.

Walker, M.R., et al., "*De Novo* Generation of Antigen-Specific CD4+CD25+ Regulatory T Cells from Human CD4+CD25− Cells,"*PNAS* 102(11):4103-4108, Mar. 15, 2005.

Walker, M.R., et al., "Induction of Antigen-Specific CD4+CD25+ Regulatory T Cells from Human CD4+CD− Cells," Benaroya Research Institute, presented at the Focus Meeting, Seattle, Washington, Jul. 2004.

Walker, M.R., et al., "Induction of FoxP3 and Acquisition of T Regulatory Activity by Stimulated Human CD4+CD25− T Cells," Benaroya Research Institute, presented at the Keystone Meeting, Seattle, Washington, Feb. 2004.

Walker, M.R., et al., "Induction of FoxP3 and Acquisition of T Regulatory Activity by Stimulated Human CD4+CD− T Cells," *Journal of Clinical Investigation* 112(9):1437-1443, Nov. 2003.

Wang, H.Y, et al., "Tumor-Specific Human CD4+ Regulatory T Cells and Their Ligands: Implications for Immunotherapy," *Immunity* 20:107-118, Jan. 2004.

Mallone, R., and G.T. Nepom, "MHC Class II Tetramers and the Pursuit of Antigen-Specific T Cells: Define, Deviate, Delete," *Clinical Immunology* 110(3):232-242, Mar. 2004.

Walker, M.R., et al., "Induction of FoxP3 and Acquisition of T Regulatory Activity by Stimulated Human CD4+CD25− T Cells," The Journal of Clinical Investigation 112(9):1437-1443, Nov. 2003.

Walker, M.R., et al., "De Novo Generation of Antigen-Specific CD4+CD25+ Regulatory T Cells From Human CD4+CD25− Cells," PNAS 102(11):4103-4108, Mar. 15, 2005.

Danke, N. A., et al., "Autoreactive T Cells in Healthy Individuals," Journal of Immunology 172(10):5967-5972, May 2004.

Danke, N. A., et al., "Comparative Study of GAD65-Specific CD4+ T Cells in Healthy and Type 1 Diabetic Subjects," Journal of Autoimmunity 25(4):303-311, Dec. 2005.

Sakaguchi, S., "The Origin of FOXP3-Expressing CD4+ Regulatory T Cells: Thymus or Periphery," Journal of Clinical Investigation 112(9):1310-1312, Nov. 2003.

Tarbell, K.V., et al., "CD25+ CD4+ T Cells, Expanded With Dendritic Cells Presenting a Single Autoantigenic Peptide, Suppress Autoimmune Diabetes," Journal of Experimental Medicine 199(11):1467-1477, Jun. 2004.

European Examination Report dated Nov. 26, 2009, issued in corresponding European Application No. 05825131.5, filed Oct. 28, 2005.

\* cited by examiner

```
                        SEQUENCE LISTING

<160> NUMBER OF SEQ ID NOS: 65

<210> SEQ ID NO 1
<211> LENGTH: 13
<212> TYPE: PRT
<213> ORGANISM: Homo Sapiens

<400> SEQUENCE: 1

Phe Phe Tyr Thr Pro Met Ser Arg Arg Glu Val Glu Asp
1               5                   10

<210> SEQ ID NO 2
<211> LENGTH: 15
<212> TYPE: PRT
<213> ORGANISM: Homo Sapiens

<400> SEQUENCE: 2

Ser His Leu Val Glu Ala Leu Tyr Leu Val Cys Gly Glu Arg Gly
1               5                   10                  15

<210> SEQ ID NO 3
<211> LENGTH: 12
<212> TYPE: PRT
<213> ORGANISM: Homo Sapiens

<400> SEQUENCE: 3

Gln Cys Cys Thr Ser Ile Cys Ser Leu Tyr Gln Leu
1               5                   10

<210> SEQ ID NO 4
<211> LENGTH: 13
<212> TYPE: PRT
<213> ORGANISM: Homo Sapiens

<400> SEQUENCE: 4
```

Asn Phe Phe Arg Met Val Ile Ser Asn Pro Ala Ala Thr
1               5                   10

<210> SEQ ID NO 5
<211> LENGTH: 13
<212> TYPE: PRT
<213> ORGANISM: Homo Sapiens

<400> SEQUENCE: 5

Ile Ala Phe Thr Ser Glu His Ser His Phe Ser Leu Lys
1               5                   10

<210> SEQ ID NO 6
<211> LENGTH: 12
<212> TYPE: PRT
<213> ORGANISM: Homo Sapiens

<400> SEQUENCE: 6

Gln His Leu Gln Lys Asp Tyr Arg Ala Tyr Thr Phe
1               5                   10

<210> SEQ ID NO 7
<211> LENGTH: 23
<212> TYPE: PRT
<213> ORGANISM: Homo Sapiens

<400> SEQUENCE: 7

Trp Tyr Val Met Val Thr Ala Ala Leu Ser Tyr Thr Ile Ser Arg Met
1               5                   10                  15

Glu Glu Ser Ser Val Thr Leu
            20

<210> SEQ ID NO 8
<211> LENGTH: 20
<212> TYPE: PRT
<213> ORGANISM: Homo Sapiens

<400> SEQUENCE: 8

His Thr Pro Gly Val His Met Ala Ser Leu Ser Val Tyr Leu Lys Thr
1               5                   10                  15

Asn Val Phe Leu
            20

<210> SEQ ID NO 9
<211> LENGTH: 18
<212> TYPE: PRT
<213> ORGANISM: Homo Sapiens

<400> SEQUENCE: 9

Met Phe Leu Arg Ser Cys Gln Gly Glu Asn Gly Thr Lys Pro Ser Phe
1               5                   10                  15

Arg Leu

<210> SEQ ID NO 10
<211> LENGTH: 18
<212> TYPE: PRT
<213> ORGANISM: Homo Sapiens

<400> SEQUENCE: 10

Thr Ala Gly Thr Thr Val Tyr Gly Ala Phe Asp Pro Leu Leu Ala Val
1               5                   10                  15

Ala Asp

```
<210> SEQ ID NO 11
<211> LENGTH: 18
<212> TYPE: PRT
<213> ORGANISM: Homo Sapiens

<400> SEQUENCE: 11

Arg Gln His Ala Arg Gln Gln Asp Lys Glu Arg Leu Ala Ala Leu Gly
1               5                   10                  15

Pro Glu

<210> SEQ ID NO 12
<211> LENGTH: 28
<212> TYPE: PRT
<213> ORGANISM: Homo Sapiens

<400> SEQUENCE: 12

Leu Ala Lys Glu Trp Gln Ala Leu Cys Ala Tyr Gln Ala Glu Pro Asn
1               5                   10                  15

Thr Cys Ala Thr Ala Gln Gly Glu Gly Asn Ile Lys
            20                  25

<210> SEQ ID NO 13
<211> LENGTH: 24
<212> TYPE: PRT
<213> ORGANISM: Homo Sapiens

<400> SEQUENCE: 13

Lys Leu Lys Val Glu Ser Ser Pro Ser Arg Ser Asp Tyr Ile Asn Ala
1               5                   10                  15

Ser Pro Ile Ile Glu His Asp Pro
            20

<210> SEQ ID NO 14
<211> LENGTH: 11
<212> TYPE: PRT
<213> ORGANISM: Homo Sapiens

<400> SEQUENCE: 14

Val Ile Val Met Leu Thr Pro Leu Val Glu Asp
1               5                   10

<210> SEQ ID NO 15
<211> LENGTH: 20
<212> TYPE: PRT
<213> ORGANISM: Homo Sapiens

<400> SEQUENCE: 15

Ser Phe Tyr Leu Lys Asn Val Gln Thr Gln Glu Thr Arg Thr Leu Thr
1               5                   10                  15

Gln Phe His Phe
            20

<210> SEQ ID NO 16
<211> LENGTH: 20
<212> TYPE: PRT
<213> ORGANISM: Homo Sapiens

<400> SEQUENCE: 16

Ser Lys Tyr Leu Ala Thr Ala Ser Thr Met Asp His Ala Arg His Gly
1               5                   10                  15

Phe Leu Pro Arg
            20
```

```
<210> SEQ ID NO 17
<211> LENGTH: 20
<212> TYPE: PRT
<213> ORGANISM: Homo Sapiens

<400> SEQUENCE: 17

Val Val His Phe Phe Lys Asn Ile Val Thr Pro Arg Thr Pro Pro Pro
1               5                   10                  15

Ser Gln Gly Lys
            20

<210> SEQ ID NO 18
<211> LENGTH: 15
<212> TYPE: PRT
<213> ORGANISM: Homo Sapiens

<400> SEQUENCE: 18

Ala His Lys Gly Phe Lys Gly Val Asp Ala Gln Thr Leu Ser Lys
1               5                   10                  15

<210> SEQ ID NO 19
<211> LENGTH: 21
<212> TYPE: PRT
<213> ORGANISM: Homo Sapiens

<400> SEQUENCE: 19

Thr Gly Thr Glu Lys Leu Ile Glu Thr Tyr Phe Ser Lys Asn Tyr Gln
1               5                   10                  15

Asp Tyr Glu Tyr Leu
            20

<210> SEQ ID NO 20
<211> LENGTH: 18
<212> TYPE: PRT
<213> ORGANISM: Homo Sapiens

<400> SEQUENCE: 20

Gly Phe Tyr Thr Thr Gly Ala Tyr Arg Gln Ile Phe Gly Asp Tyr Leu
1               5                   10                  15

Thr Thr

<210> SEQ ID NO 21
<211> LENGTH: 13
<212> TYPE: PRT
<213> ORGANISM: Homo Sapiens

<400> SEQUENCE: 21

His Cys Leu Gly Lys Trp Leu Gly His Pro Asp Lys Phe
1               5                   10

<210> SEQ ID NO 22
<211> LENGTH: 20
<212> TYPE: PRT
<213> ORGANISM: Homo Sapiens

<400> SEQUENCE: 22

Glu Val Gly Trp Tyr Arg Pro Pro Phe Ser Arg Val Val His Leu Tyr
1               5                   10                  15

Arg Asn Gly Lys
            20

<210> SEQ ID NO 23
<211> LENGTH: 13
<212> TYPE: PRT
```

-continued

<213> ORGANISM: Homo Sapiens

<400> SEQUENCE: 23

Thr Cys Phe Phe Arg Asp His Ser Tyr Gln Glu Glu Ala
1               5                   10

<210> SEQ ID NO 24
<211> LENGTH: 9
<212> TYPE: PRT
<213> ORGANISM: Homo Sapiens

<400> SEQUENCE: 24

Phe Val Ile Val Pro Val Leu Gly Pro
1               5

<210> SEQ ID NO 25
<211> LENGTH: 14
<212> TYPE: PRT
<213> ORGANISM: Homo Sapiens

<400> SEQUENCE: 25

Ala Gly Ile Ala Gly Phe Lys Gly Glu Gln Gly Pro Lys Gly
1               5                   10

<210> SEQ ID NO 26
<211> LENGTH: 14
<212> TYPE: PRT
<213> ORGANISM: Homo Sapiens

<400> SEQUENCE: 26

Gly Gly Val Gly Pro Ile Gly Pro Pro Gly Glu Arg Gly Ala
1               5                   10

<210> SEQ ID NO 27
<211> LENGTH: 19
<212> TYPE: PRT
<213> ORGANISM: Homo Sapiens

<400> SEQUENCE: 27

Ser Gly Phe Gln Gly Leu Pro Gly Pro Pro Gly Pro Pro Gly Glu Gly
1               5                   10                  15

Gly Gly Lys

<210> SEQ ID NO 28
<211> LENGTH: 18
<212> TYPE: PRT
<213> ORGANISM: Homo Sapiens

<400> SEQUENCE: 28

Arg Gly Phe Thr Gly Leu Gln Gly Leu Pro Gly Pro Pro Gly Pro Ser
1               5                   10                  15

Gly Asp

<210> SEQ ID NO 29
<211> LENGTH: 13
<212> TYPE: PRT
<213> ORGANISM: Homo Sapiens

<400> SEQUENCE: 29

Ser Ala Val Arg Ala Arg Ser Ser Val Pro Gly Val Arg
1               5                   10

<210> SEQ ID NO 30
<211> LENGTH: 13

```
<212> TYPE: PRT
<213> ORGANISM: Homo Sapiens

<400> SEQUENCE: 30

Arg Ser Phe Thr Leu Ala Ser Ser Glu Thr Gly Val Gly
1               5                   10

<210> SEQ ID NO 31
<211> LENGTH: 12
<212> TYPE: PRT
<213> ORGANISM: Homo Sapiens

<400> SEQUENCE: 31

Ala Gly Trp Leu Ala Asp Arg Ser Val Arg Tyr Pro
1               5                   10

<210> SEQ ID NO 32
<211> LENGTH: 33
<212> TYPE: PRT
<213> ORGANISM: Homo Sapiens

<400> SEQUENCE: 32

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 33
<211> LENGTH: 14
<212> TYPE: PRT
<213> ORGANISM: Homo Sapiens

<400> SEQUENCE: 33

Pro Glu Gln Pro Gln Gln Ser Phe Pro Glu Gln Glu Arg Pro
1               5                   10

<210> SEQ ID NO 34
<211> LENGTH: 12
<212> TYPE: PRT
<213> ORGANISM: Homo Sapiens

<400> SEQUENCE: 34

Ser Gly Gln Gly Ser Phe Gln Pro Ser Gln Gln Asn
1               5                   10

<210> SEQ ID NO 35
<211> LENGTH: 36
<212> TYPE: PRT
<213> ORGANISM: Homo Sapiens

<400> SEQUENCE: 35

Ser Gly Gln Gly Gln Arg Pro Gly Gln Trp Leu Gln Pro Gly Gln Gly
1               5                   10                  15

Gln Gln Gly Tyr Tyr Pro Thr Ser Pro Gln Gln Ser Gly Gln Gly Gln
            20                  25                  30

Gln Leu Gly Gln
            35

<210> SEQ ID NO 36
<211> LENGTH: 17
<212> TYPE: PRT
<213> ORGANISM: Homo Sapiens
```

-continued

```
<400> SEQUENCE: 36

Gln Ala Thr Gln Lys Ile Thr Tyr Arg Ile Ser Gly Val Gly Ile Asp
1               5                   10                  15

Gln

<210> SEQ ID NO 37
<211> LENGTH: 17
<212> TYPE: PRT
<213> ORGANISM: Homo Sapiens

<400> SEQUENCE: 37

Pro Phe Gly Ile Phe Val Val Asp Lys Asn Thr Gly Asp Ile Asn Ile
1               5                   10                  15

Thr

<210> SEQ ID NO 38
<211> LENGTH: 17
<212> TYPE: PRT
<213> ORGANISM: Homo Sapiens

<400> SEQUENCE: 38

His Leu Asn Ser Lys Ile Ala Phe Lys Ile Val Ser Gln Glu Pro Ala
1               5                   10                  15

Gly

<210> SEQ ID NO 39
<211> LENGTH: 17
<212> TYPE: PRT
<213> ORGANISM: Homo Sapiens

<400> SEQUENCE: 39

Gly Thr Pro Met Phe Leu Leu Ser Arg Asn Thr Gly Glu Val Arg Thr
1               5                   10                  15

Leu

<210> SEQ ID NO 40
<211> LENGTH: 17
<212> TYPE: PRT
<213> ORGANISM: Homo Sapiens

<400> SEQUENCE: 40

Gln Cys Glu Cys Asn Ile Lys Val Lys Asp Val Asn Asp Asn Phe Pro
1               5                   10                  15

Met

<210> SEQ ID NO 41
<211> LENGTH: 17
<212> TYPE: PRT
<213> ORGANISM: Homo Sapiens

<400> SEQUENCE: 41

Ser Val Lys Leu Ser Ile Ala Val Lys Asn Lys Ala Glu Phe His Gln
1               5                   10                  15

Ser

<210> SEQ ID NO 42
<211> LENGTH: 17
<212> TYPE: PRT
<213> ORGANISM: Homo Sapiens

<400> SEQUENCE: 42
```

Asn Val Arg Glu Gly Ile Ala Phe Arg Pro Ala Ser Lys Thr Phe Thr
1               5                   10                  15

Val

<210> SEQ ID NO 43
<211> LENGTH: 19
<212> TYPE: PRT
<213> ORGANISM: Homo Sapiens

<400> SEQUENCE: 43

Glu Trp Ile Lys Phe Ala Ala Cys Arg Glu Gly Glu Asp Asn Ser Lys
1               5                   10                  15

Arg Asn Pro

<210> SEQ ID NO 44
<211> LENGTH: 18
<212> TYPE: PRT
<213> ORGANISM: Homo Sapiens

<400> SEQUENCE: 44

Ile Pro Asn Ile Met Phe Phe Ser Thr Met Lys Arg Pro Ser Arg Glu
1               5                   10                  15

Lys Gln

<210> SEQ ID NO 45
<211> LENGTH: 19
<212> TYPE: PRT
<213> ORGANISM: Homo Sapiens

<400> SEQUENCE: 45

Ile Thr Asp Asn Pro Tyr Met Thr Ser Ile Pro Val Asn Ala Phe Gln
1               5                   10                  15

Gly Leu Cys

<210> SEQ ID NO 46
<211> LENGTH: 16
<212> TYPE: PRT
<213> ORGANISM: Homo Sapiens

<400> SEQUENCE: 46

Leu Asn Lys Asn Lys Tyr Leu Thr Val Ile Asp Lys Asp Ala Phe Gly
1               5                   10                  15

<210> SEQ ID NO 47
<211> LENGTH: 16
<212> TYPE: PRT
<213> ORGANISM: Homo Sapiens

<400> SEQUENCE: 47

Ser Val Thr Ala Leu Pro Ser Lys Gly Leu Glu His Leu Lys Glu Leu
1               5                   10                  15

<210> SEQ ID NO 48
<211> LENGTH: 16
<212> TYPE: PRT
<213> ORGANISM: Homo Sapiens

<400> SEQUENCE: 48

His Leu Lys Glu Leu Ile Ala Arg Asn Thr Trp Thr Leu Lys Lys Leu
1               5                   10                  15

<210> SEQ ID NO 49
<211> LENGTH: 20

-continued

<210> SEQ ID NO 49
<211> LENGTH: (implied)
<212> TYPE: PRT
<213> ORGANISM: Homo Sapiens

<400> SEQUENCE: 49

Phe Gln Asp Thr His Asn Asn Ala His Tyr Tyr Val Phe Phe Glu Glu
1               5                   10                  15

Gln Glu Asp Glu
            20

<210> SEQ ID NO 50
<211> LENGTH: 20
<212> TYPE: PRT
<213> ORGANISM: Homo Sapiens

<400> SEQUENCE: 50

Glu Glu Gln Glu Asp Glu Ile Ile Gly Phe Gly Gln Glu Leu Lys Asn
1               5                   10                  15

Pro Gln Glu Glu
            20

<210> SEQ ID NO 51
<211> LENGTH: 11
<212> TYPE: PRT
<213> ORGANISM: Homo Sapiens

<400> SEQUENCE: 51

Arg Ile Met Pro Glu Asp Ile Ile Ile Asn Cys
1               5                   10

<210> SEQ ID NO 52
<211> LENGTH: 20
<212> TYPE: DNA
<213> ORGANISM: Homo Sapiens

<400> SEQUENCE: 52
ccacatcgct cagacaccat                                          20

<210> SEQ ID NO 53
<211> LENGTH: 26
<212> TYPE: DNA
<213> ORGANISM: Homo Sapiens

<400> SEQUENCE: 53
ggcaacaata tccactttac cagagt                                   26

<210> SEQ ID NO 54
<211> LENGTH: 23
<212> TYPE: DNA
<213> ORGANISM: Homo Sapiens

<400> SEQUENCE: 54
gaaacagcac attcccagag ttc                                      23

<210> SEQ ID NO 55
<211> LENGTH: 17
<212> TYPE: DNA
<213> ORGANISM: Homo Sapiens

<400> SEQUENCE: 55
atggcccagc ggatgag                                             17

<210> SEQ ID NO 56
<211> LENGTH: 27
<212> TYPE: DNA

<213> ORGANISM: Homo Sapiens

<400> SEQUENCE: 56
agaattcatg gccataagtg gagtccc            27

<210> SEQ ID NO 57
<211> LENGTH: 32
<212> TYPE: DNA
<213> ORGANISM: Homo Sapiens

<400> SEQUENCE: 57
ccaggtctgc tgacgactct gtagtctctg gg      32

<210> SEQ ID NO 58
<211> LENGTH: 27
<212> TYPE: DNA
<213> ORGANISM: Homo Sapiens

<400> SEQUENCE: 58
agaattcatg gccataagtg gagtccc            27

<210> SEQ ID NO 59
<211> LENGTH: 25
<212> TYPE: DNA
<213> ORGANISM: Homo Sapiens

<400> SEQUENCE: 59
ctggtaccat cctactgggc gagtt              25

<210> SEQ ID NO 60
<211> LENGTH: 29
<212> TYPE: DNA
<213> ORGANISM: Homo Sapiens

<400> SEQUENCE: 60
actcgagcca tggtgtgtct gaagttccc          29

<210> SEQ ID NO 61
<211> LENGTH: 26
<212> TYPE: DNA
<213> ORGANISM: Homo Sapiens

<400> SEQUENCE: 61
ccaggtctgc tgacgacttg ctctgt             26

<210> SEQ ID NO 62
<211> LENGTH: 29
<212> TYPE: DNA
<213> ORGANISM: Homo Sapiens

<400> SEQUENCE: 62
actcgagcca tggtgtgtct gaagttccc          29

<210> SEQ ID NO 63
<211> LENGTH: 29
<212> TYPE: DNA
<213> ORGANISM: Homo Sapiens

<400> SEQUENCE: 63
acaagcttgc ctgagccagt tccttttcc          29

<210> SEQ ID NO 64
<211> LENGTH: 27
<212> TYPE: DNA

-continued

```
<213> ORGANISM: Homo Sapiens

<400> SEQUENCE: 64
agaattcatg gtgtgtctga agttccc                                      27

<210> SEQ ID NO 65
<211> LENGTH: 29
<212> TYPE: DNA
<213> ORGANISM: Homo Sapiens

<400> SEQUENCE: 65
ctggtaccrt agtgccattc gattttctg                                    29
```

METHODS OF GENERATING ANTIGEN-SPECIFIC CD4+CD25+REGULATORY T CELLS, COMPOSITIONS AND METHODS OF USE

CROSS-REFERENCE(S) TO RELATED APPLICATION(S)

This application claims the benefit of U.S. Provisional Application Ser. No. 60/623,380, filed Oct. 29, 2004, which is herein incorporated by reference.

STATEMENT OF GOVERNMENT LICENSE RIGHTS

This invention was made with government support under DK63423 awarded by the National Institutes of Health. The government has certain rights in the invention.

FIELD OF THE INVENTION

The present invention relates to novel methods of generating antigen-specific regulatory T cells which can be used for therapeutic purposes.

BACKGROUND OF THE INVENTION

Immune tolerance is central to the immune system's ability to differentiate between self and foreign proteins. Central tolerance is initially achieved during thymic selection by the deletion of self-reactive T cells. However, central tolerance is incomplete, and further immune regulation is required in the periphery. Peripheral mechanisms of T cell regulation include the induction of anergy, activation induced cell death, and regulatory T cells.

Within the CD4+ T lymphocyte cell population, three categories of regulatory T cells have been described: TH3 cells, Type 1 regulatory (Tr1) cells, and CD4+CD25+ T regulatory cells ("Treg"). TH3 cells function via the secretion of TGF-β and can be generated in vitro by stimulation in the presence of IL-4 or in vivo through oral administration of low dose antigens (Chen et al., *Science* 265:1237-1240, 1994; Inobe et al., *Eur. J. Immunol.* 28:2780-2790, 1998). Type 1 regulatory T cells (Tr1) suppress T cells through the production of IL-10 and TGF-β and are derived by stimulation of memory T cells in the presence of IL-10 (Groux et al., *Nature* 389:737-742, 1996; Groux et al., *J. Exp. Med.* 184:19-29, 1996). CD4+ CD25+ regulatory T cells (Treg) are thought to function as a regulator of autoimmunity by suppressing the proliferation and/or cytokine production of CD4+CD25– T cell responder cells at the site of inflammation.

CD4+CD25+ Treg cells are known to be present in both humans and mice and are characterized by expression of CD25 (for review, see Sakaguchi et al., *Immunol. Rev.* 182:18-32). Treg cells isolated from human peripheral blood are highly differentiated memory cells based on their FACS staining characteristics and short telomere length and historically are thought to be derived from the thymus (Taams et al., *Eur. J. Immunol.* 32:1621-1630, 2002; Jonuleit et al., *J. Exp. Med.* 193:1285-1294, 2001). In humans, Tregs are believed to represent 1-3% of all CD4+ T cells and require activation to induce suppressor function. The suppressive function of these Treg cells is mediated via cell-cell contact and is abrogated by the addition of IL-2 (Baecher-Allan et al., *J. Immunol* 167:1245-1253, 2001).

The Treg population is reduced in autoimmune-prone animals and humans (see Salomon et al., *Immunity* 12:431-440, 2000; Kukreja et al., *J. Clin. Invest.* 109:131-140, 2002). Mice carrying the X-linked scurfy mutation develop a multi-organ autoimmune disease and lack conventional CD4+ CD25+regulatory T cells (Fontenot et al., *Nat. Immunol.* 4:330-336, 2003; Khattri et al., *Nat. Immunol.* 4:337-342, 2003). It has been shown that the gene mutated in these mice is FoxP3 which encodes a member of the forkhead/winged helix family and acts as a transcriptional repressor (Schubert et al., *J. Biol. Chem.* 276:37672-37679, 2001). In mice, FoxP3 has been shown to be expressed exclusively in CD4+ CD25+ Treg cells and is not induced upon activation of CD25– cells. However, when FoxP3 is introduced via retrovirus or via transgene expression, naïve CD4+CD25– T cells are converted to Treg cells (Hori et al., *Science* 299:1057-1061, 2003). In humans, it has been noted that mutations in FoxP3 lead to a severe lymphoproliferative disorder known as IPEX (immunodysregulation, polyendocrinopathy, enteropathy, X-linked) syndrome, characterized by lymphoproliferative disease, insulin-dependent diabetes, thyroiditis, eczema and death at an early age (see Wildin et al., *J. Med. Genet.* 39:537-545, 2002).

Due to their low frequency in peripheral blood, freshly isolated human CD4+CD25+ T cells with suppressive function are difficult to isolate and expand. In the autoimmune NOD mouse model, in which mice are transgenic for a single T cell receptor, one group of investigators has recently isolated naturally occurring antigen-specific Treg cells from mouse spleen and lymph nodes, expanded the cells and demonstrated that transfer of these cells to the diabetic prone NOD mouse can suppress the development of diabetes (Tang et al., *J. Exp. Med.* 199:1455-1465, 2004, Masteller et al., *J. Immunol* 175:3053-3059, 2005; Tarbell et al., *J. Exp Med* 199:1467-1477, 2004). This approach demonstrates the therapeutic benefit of Treg transfer to treat autoimmune disease. However, the approach used in the NOD mouse model is not therapeutically applicable to human subjects, due to the requirement that a large number of rare CD4+CD25+ T cells (approximately 4% of circulating T cells) be isolated from the peripheral blood. Further, this mouse model contains a single fixed T cell receptor (TCR) and does not address the problem of following TCR repertoire evolution or identifying antigen-specific T cells in complex systems where a polyclonal T cell response is present. Similar studies have not been possible in human subjects due to the low frequency of antigen-specific Treg cells circulating in the peripheral blood, especially with respect to autoreactive T cells.

Given the important role CD4+CD25+ regulatory T cells play in immune tolerance, there is a need to develop methods for generating, selecting and expanding human antigen-specific regulatory CD4+CD25+ T cells from the peripheral blood of a subject in need thereof for use in the treatment and/or prevention of autoimmune diseases, inflammatory conditions and for the prevention of graft rejection in a recipient following solid organ or stem cell transplantation.

SUMMARY OF THE INVENTION

In accordance with the foregoing, in one aspect, the present invention provides a method for generating a T cell population comprising antigen-specific CD4+CD25+ regulatory T cells from freshly isolated CD4+CD25– T cells. The method comprises isolating CD4+CD25– T cells from a sample comprising T cells obtained from a mammalian subject; determining the MHC Class II type of the subject; producing antigen-specific regulatory T cells by contacting the isolated CD4+ CD25– T cells in a culture vessel with a CD4+CD25+ induction agent for a time period sufficient to produce antigen-specific CD4+CD25+ regulatory T cells; and selecting the CD4+CD25+ antigen-specific regulatory T cells by sorting the cells in the induction culture with a selection agent comprising at least one artificial multimeric MHC Class II/peptide complex, wherein the MHC Class II/peptide complex is chosen to correspond to the MHC Class II type of the subject.

In another aspect, the invention provides pharmaceutical compositions comprising a population of isolated mammalian antigen-specific regulatory T cells characterized by the expression of CD4+, CD25+ and FoxP3, wherein from about 5% to about 20% of the cell population is capable of specifically binding to an artificial MHC Class II/peptide complex. In some embodiments, the pharmaceutical compositions comprise a population of isolated mammalian antigen-specific regulatory T cells characterized by the expression of CD4+, CD25+ and FoxP3, wherein greater than 80% of the T cell population is capable of specifically binding to an artificial MHC Class II/peptide complex.

In yet another aspect, the present invention provides a method for treating and/or preventing an autoimmune disease in a mammalian subject in need thereof. The method comprises obtaining a sample containing T cells from the subject and determining the MHC Class II type of the subject. A population of CD4+CD25− T cells is isolated from the sample and antigen-specific regulatory T cells are produced by contacting the isolated T cells in a culture vessel with an induction agent. In some embodiments, the induction agent comprises a peptide derived from a self-antigen associated with an autoimmune disease and a population of antigen presenting cells that are MHC Class II matched to the subject. The cells in the induction culture are then sorted with at least one MHC Class II/peptide complex, wherein the MHC Class II is matched to the MHC Class II type of the subject, and wherein the peptide is cognate with the induction agent. In some embodiments, the sorted cells are then expanded in a culture vessel, and administered in an amount effective to treat and/or prevent the autoimmune disease in the subject.

In another aspect, the present invention provides a method of reducing the risk and/or the severity of an adverse immune response in a patient that has undergone, is undergoing, or will undergo, an organ or tissue transplant. The method comprises obtaining a sample containing T cells from the patient and determining the MHC Class II of the patient. A population of CD4+CD25− T cells is isolated from the sample and transplant-specific regulatory T cells are produced by contacting the isolated T cells in a culture vessel with an induction agent. In some embodiments, the induction agent comprises at least one antigenic peptide specific to the transplant organ or tissue and a population of antigen presenting cells that are MHC Class II matched to the patient. The cells in the induction culture are sorted with at least one MHC Class II/peptide complex, wherein the peptide is cognate with the induction agent. In some embodiments, the sorted cells are then expanded in a culture vessel, and administered in an amount effective to reduce the risk and/or the severity of an adverse immune response in the patient.

Using the methods and compositions according to these aspects of the present invention, peripherally derived Treg cells can be generated for use as an immunotherapeutic agent to modulate an in vivo immune response to either a foreign or a self-antigen.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
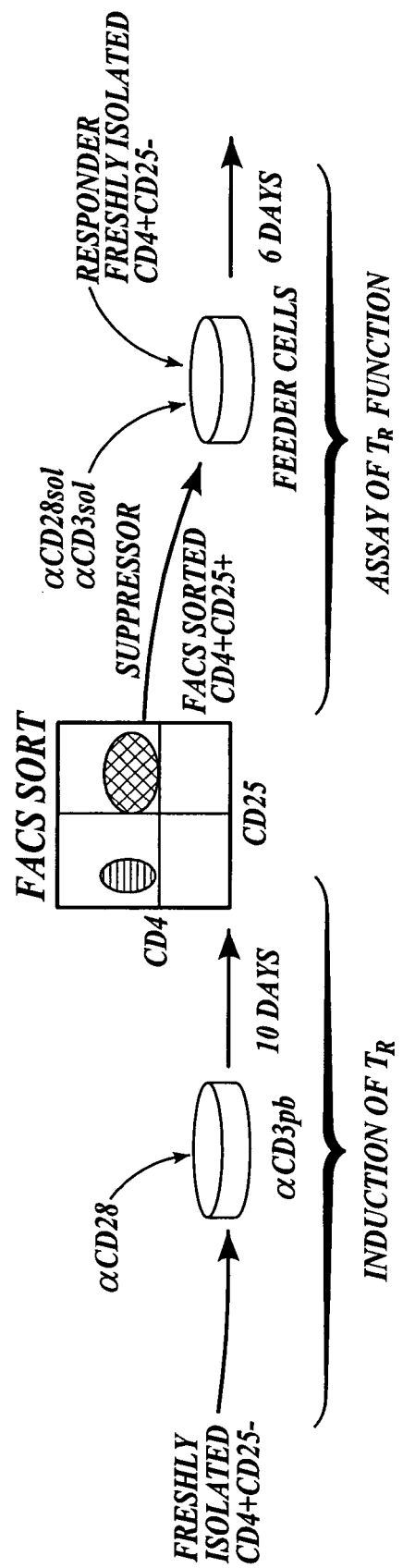
FIG. 1 is a schematic diagram illustrating a method of generating CD4+CD25+ regulatory T cells in an ex vivo culture system from CD4+CD25− cells with anti-CD3 and anti-CD28 induction agents in accordance with an embodiment of the present invention.

Unless specifically defined herein, all terms used herein have the same meaning as they would to one skilled in the art of the present invention. The following definitions are provided in order to provide clarity with respect to the terms as they are used in the specification and claims to describe the present invention.

As used herein, the term "regulatory T cells" or "Treg" cells refers to T cells which express the cell surface markers CD4+ and CD25+, which express FoxP3 protein as measured by a Western blot and/or FoxP3 mRNA transcript and are IL-10 and TGF-β independent, as measured in vitro.

As used herein, the term "MHC Class II/peptide complex" refers to a complex comprising a peptide having an amino acid sequence that is cognate (e.g., identical or related to) at least one antigen in the induction culture. Any form of MHC Class II/peptide complex capable of binding T cells specific for the cognate antigen is intended to be within the scope of the present invention, including monomer, dimer, and multimer (e.g., tetramer) forms of MHC/peptide complexes, as well as MHC/peptide complexes attached to a surface, soluble MHC/peptide complexes, and MHC/peptide complexes included in a lipid bilayer (e.g., artificial APCs).

As used herein, the term "Tmr+" refers to a T cell population that has been sorted by a MHC Class II/peptide complex.

As used herein, the term "antigen-specific regulatory T cells" or "antigen-specific Tregs" refers to Treg cells which were induced in the presence of an antigen and which express the cell surface markers CD4+ and CD25+, which express FoxP3 protein as measured by a Western blot and/or FoxP3 mRNA transcript and are IL-10 and TGF-β independent, as measured in vitro. In an in vitro proliferation assay, after re-exposure to the cognate antigen used for induction, antigen-specific regulatory T cells are capable of actively suppressing the proliferation of freshly isolated CD4+CD25− T responder cells which have been stimulated in culture with an activating signal.

As used herein, the term "suppressor function" refers to the ability of a Treg cell to suppress the level of proliferation of a freshly isolated CD4+CD25− responder T cell population in a co-culture in response to an antigen as compared to the proliferation of CD4+CD25− in response to the antigen without the Treg cells, as measured in an in vitro assay.

As used herein, the term "responder T cell," or "R" refers to freshly isolated CD4+CD25− T cells which normally proliferate in response to an activating signal.

As used herein, the term "tolerance" includes refractivity to activating receptor-mediated stimulation. Such refractivity is generally antigen-specific and persists after exposure to the tolerizing antigen has ceased. For example, tolerance is characterized by lack of cytokine production, e.g., IL-2. Tolerance can occur to self antigens or to foreign antigens.

As used herein, the term "self-antigen" refers to an immunogenic antigen or epitope which is native to a mammal and which may be involved in the pathogenesis of an autoimmune disease.

As used herein, the term "derived from" or "a derivative thereof" in the context of peptide or polypeptide sequences, means that the peptide or polypeptide is not limited to the specific sequence described, but also includes variations in that sequence, which may include amino acid additions, deletions, substitutions or modifications to the extent that the variations in the listed sequence retain the ability to modulate an immune response.

As used herein, the term "peptide" or "polypeptide" is a linked sequence of amino acids and may be natural, recombinant, synthetic or a modification or combination of natural, synthetic, and recombinant.

As used herein the term "treating" refers to preventing, suppressing, repressing or eliminating the disease or inflammatory condition. Preventing the disease or condition involves administering a composition of the present invention to a subject prior to onset of the disease. Suppressing the disease or condition involves administering a composition of the present invention to a subject after induction of the disease or condition but before its clinical appearance. Repressing a disease or condition involves administering a composition of the present invention to a subject after clinical appearance of the disease or condition.

As used herein, the expression "therapeutically effective amount" refers to an amount of the composition which is effective to achieve a desired therapeutic result, such as, for example, the prevention, amelioration or prophylaxis of an autoimmune disease or inflammatory condition.

As used herein, an "autoimmune disease" is a disease or disorder arising from and directed against an individual's own tissues. Examples of autoimmune diseases or disorders include, but are not limited to arthritis (rheumatoid arthritis, juvenile rheumatoid arthritis, psoriatic arthritis), conditions involving infiltration of T cells and chronic inflammatory responses, autoimmune myocarditis, multiple sclerosis, pemphigus, and type 1 diabetes (also referred to as insulin-dependent diabetes mellitus (IDDM)). Additional examples of autoimmune diseases are provided in TABLES 1 and 2.

As used herein, the term "organ or tissue transplant" refers to any solid organ such as kidneys, heart, lungs, liver, and pancreas including tissue grafts, and whole or selected populations of blood or bone marrow transplants.

In one aspect, the present invention provides a method for generating an antigen-specific CD4+CD25+regulatory T cell population from freshly isolated CD4+CD25-T cells. The method comprises isolating CD4+CD25− T cells from a sample comprising T cells obtained from a mammalian subject; determining the MHC Class II type of the subject; inducing the generation of antigen-specific regulatory T cells by contacting the isolated CD4+CD25− T cells in a culture vessel with a CD4+CD25+induction agent for a period of time sufficient to generate CD4+CD25+ regulatory T cells; and selecting the CD4+CD25+ antigen-specific regulatory T cell population by sorting the cells in the induction culture with a selection agent comprising at least one MHC Class II/peptide complex, wherein the MHC Class II/peptide complex is chosen to correspond to the MHC Class II type of the subject.

Mammalian T cells for use in the method of the invention may be isolated from a biological sample taken from a mammalian subject, such as a human subject, originating from a number of sources, including for example, peripheral blood mononuclear cells, bone marrow, thymus, tissue biopsy, tumor, lymph node tissue, gut associated lymphoid tissue, mucosa associated lymph node tissue, spleen tissue or any other lymphoid tissue and tumors. In a preferred embodiment, human T cells are isolated as peripheral blood mononuclear cells (PBMC) from a blood sample obtained from the peripheral blood of a subject. T cells may also be obtained from a unit of blood obtained from an apheresis or leukapheresis procedure.

A population of CD4+CD25− cells may be isolated from a sample comprising human T cells through the use of gradients and positive/negative selection techniques well known to those of skill in the art. For example, PBMC can be partially purified by density gradient centrifugation (e.g., through a Ficoll-Hypaque gradient), by panning, affinity separation, cell sorting (e.g., using antibodies specific for one or more cell surface markers, such as anti-CD4 and anti-CD25 antibodies) and other techniques that provide enrichment of CD4+CD25− cells. An exemplary method for isolating CD4+CD25− cells is described in Example 1. After selection, the enriched CD4+CD25− cell population is preferably at least 95% CD25−, more preferably at least 99% CD25−, more preferably at least 99.9% CD25−, up to 100% CD25−.

In one embodiment, the isolated CD4+CD25− T cell population is enriched for memory T cells by sorting for CD45+RO+ cell surface markers. An exemplary method for selecting CD4+CD25−CD45+RO+ T cells is described in Example 2. In another embodiment, the selected CD4+CD25− T cell population is enriched for naïve T cells by sorting for CD45+RA+ cell surface markers. An exemplary method for selecting CD4+CD25−CD45+RA+ T cells is described in Example 2.

The isolated CD4+CD25− T cell population is induced in a culture vessel to generate CD4+CD25+T regulatory cells by incubating the isolated CD25− cells with a CD4+CD25+ induction agent for a period of time sufficient to generate CD4+CD25+ Treg cells. In some embodiments, the CD4+CD25+ induction agent comprises one or more antigenic peptides and antigen presenting cells that are MHC Class II matched to the source of T cells and are capable of generating antigen-specific Treg cells that are CD4+CD25+, FoxP3+ and capable of suppressing freshly isolated responder T cells as further described herein. In some embodiments, the CD4+CD25+ induction agent further comprises stimulatory molecules such as, for example, anti-CD3 and/or anti-CD28 antibodies, and/or artificial MHC/peptide complexes as described herein.

Whole antigenic proteins, portions thereof, or antigenic peptides may be added to the induction culture in any suitable form, such as isolated peptides, peptides naturally expressed by the antigen presenting cells, or recombinantly expressed by the antigen presenting cells. The antigen presenting cells or ("APCs") may be any type of cell, such as for example, dendritic cells or macrophages that are capable of taking up antigens, including antigenic peptides, processing them to small peptides and expressing them on their cell surface in the proper MHC Class II context for presentation to T cells. The antigen presenting cells may be autologous, (e.g., derived from the subject), or the antigen presenting cells may be heterologous cells that are MHC matched to the source of CD4+ T cells. Exemplary methods of obtaining antigen presenting cells that are useful in the practice of the methods of the invention are provided herein in Example 1 and Example 3.

In a preferred embodiment, the CD4+CD25+ induction agent comprises antigen presenting cells autologous with the source of CD4+CD25− T cells and at least one antigenic peptide chosen to induce a population of antigen-specific CD4+CD25+regulatory T cells. In accordance with this embodiment, multiple antigenic peptides may be present in one induction culture having the same peptide sequence or having different peptide sequences. In accordance with this embodiment, the antigenic protein from which the antigenic peptides are derived is chosen according to the desired antigen specificity of the ex vivo generated regulatory T cells. As further described below, the chosen antigenic protein may be a self-antigen associated with an inflammatory or autoimmune pathology; or the antigenic protein may be chosen to control an undesirable immune response, (e.g., to avoid transplant rejection).

Once the antigenic protein is chosen, the choice of the antigenic peptide from among the amino acids comprising the antigenic protein depends in part on the binding properties of the MHC Class II type of the subject, the particular disease of interest, and the interactions of specific amino acids derived from an antigenic protein with a T cell receptor. In accordance with some embodiments of the present invention, the antigenic protein and peptide derived therefrom is chosen in reference to the MHC Class type of the subject. The MHC Class II type for the sample in question may be determined using standard techniques, such as for example, an SSO based typing method (e.g., HLA-DRB and HLA-DQB SSO typing kits from Dynal Biotech LLC, Brown Deer, Wis.) or using sequence based HLA typing methods. Alternatively, the MHC Class II type of a particular subject may be obtained by referral to the subject's medical history.

For certain diseases, a correlation is known to exist between particular MHC Class II type alleles and disease susceptibility as shown below in TABLE 1 and discussed in more detail below.

In some embodiments, the chosen antigenic peptide is derived from a self-antigen. The self-antigen may be any tissue-specific antigen, including proteins known to be associated with, or found to be involved in, T cell-mediated disease, such as an autoimmune disease or an inflammatory condition. The self-antigen may be a protein or fragment, a variant, analog, homolog or derivative thereof. An exemplary method of generating antigen-specific Tregs using peptides derived from the self-antigen GAD65 is provided herein (see Example 6).

In other embodiments, the chosen antigenic peptide is derived from a foreign antigen. The foreign antigen may be any protein known to be associated with, or found to be involved in, T cell-mediated disease or inflammatory condition. For example, a foreign antigen may be expressed on allogeneic cells derived from a source other than the subject, such as, for example, in the context of transplantation (e.g., such as a solid organ transplant or bone marrow transplant). Alternatively, a foreign antigen may be added to the induction culture along with antigen presenting cells autologous to the source of T cells. The antigen-specific Treg cells generated using a foreign antigen may be used to modulate an undesired T cell-mediated response against a foreign antigen. An exemplary method of generating antigen-specific Tregs using peptides derived from the foreign antigen hemagluttanin (HA) is provided herein (see Example 5).

The peptides derived from self-antigens or foreign antigens may be, for example, from about 9 to about 20 amino acids or more in length, more preferably about 9-10 amino acids in length. The peptides for use in the methods of the invention may be prepared in a variety of ways. For example, peptides may be synthesized using an automated synthesizer (see, e.g., Hunkapiller et al., Nature 310:105-111, 1984; and Bodanszky, *Principles of Peptide Synthesis*, Springer Verlag, 1984). Alternatively, peptides may be synthesized by proteolytic cleavage (e.g., by trypsin, chymotrypsin, papain, V8 protease, and the like) or specific chemical cleavage (e.g., by cyanogen bromide). The peptides may also be synthesized by expression of nucleic acid sequences encoding a particular peptide. Exemplary antigenic proteins that may be used as induction agents in the method of this aspect of the invention are provided below in TABLE 2.

In accordance with the method of this aspect of the invention, the CD4+CD25− T cells are contacted with a CD4+CD25+ induction agent in an amount and for a time period sufficient to generate CD4+CD25+ Treg cells. The time period of induction sufficient to generate CD4+CD25+ regulatory T cells in accordance with this aspect of the invention may be determined by assaying the induction culture for the presence of CD25+cells. In one representative embodiment, the time period ranges from about 8 to about 12 days or longer. In a preferred embodiment, the time period of the induction culture ranges from about 9 days to about 11 days. The specific amount of induction agent used will vary according to a number of factors that will be appreciated by those of skill in the art, including, for example, the origin of the CD4+CD25− cells to be induced, the potency and other characteristics of the CD4+CD25+ induction agent used. In some embodiments, it is currently preferred that the induction agent in the form of a peptide is used at a concentration of from about 1 µg/ml to about 100 µg/ml and more preferably about 5 µg/ml to about 20 µg/ml.

At the end of the induction culture period, the antigen-specific Treg cells are selected on the basis of the expression of the CD25+marker and/or binding to an artificial MHC Class II/peptide complex. In a preferred embodiment, the artificial MHC Class II/peptide complex is a tetramer complex chosen to correspond to the MHC Class II type of the T cell source and the antigenic peptide present in the CD4+CD25+ induction agent. The cells in the induction culture are contacted with the artificial MHC Class II/peptide complexes, incubated for a period of time sufficient to bind to the Treg cells, then FACS sorted to obtain a T cell population comprising CD4+CD25+Tmr+ cells.

It has been shown that soluble MHC Class II molecules, when occupied with a particular peptide, will bind selectively to T cells specific for that MHC/peptide complex. The development of fluorescently labeled MHC Class II/peptide staining reagents allows one to directly detect and isolate antigen-specific T cells, independent of cellular function as described in U.S. Application Publication No. 2003/0073102 A1 published Apr. 17, 2003, the disclosure of which is incorporated herein by reference.

In accordance with the methods of this aspect of the invention, the artificial MHC/peptide complex comprises a peptide having an amino acid sequence that is cognate (e.g., identical or related to) the antigen contained in the induction culture. Any form of MHC Class II/peptide complex capable of binding T cells specific for the cognate antigen may be used in the methods of the present invention. For example, monomer, dimer, and multimer (e.g., such as tetramer) forms of MHC/peptide complexes may be used. MHC/peptide complex pools may also be used, wherein the pool comprises a set of cognate peptides corresponding to the set of peptides present in the induction culture. The MHC/peptide complexes may be attached to a surface, such as a bead or plate, or may be soluble. The peptides present in the complex may be either covalently (e.g., by crosslinking or recombinant expression) or noncovalently attached to the MHC Class II molecules. In one embodiment, the recombinant artificial MHC/peptide complexes are included in artificial membrane bilayers containing discrete membrane microdomains, such as described for artificial antigen presenting cells (aAPCs) (Mallet-Designe et al., *J. Immunol.* 170:123-131, 2003).

One form of artificial MHC/peptide complex that is particularly useful in the practice of one embodiment of the method according to this aspect of the invention is a multimer complex (also termed tetramer) that utilizes avidin to couple together four biotin labeled MHC molecules containing a relevant peptide. By having four MHC molecules, the affinity for reaction with the T cell receptors is increased. Such molecular complexes are labeled with fluorescent dyes and are able to bind the T cell receptors specific for the restricting MHC type and the peptide. Using MHC/peptide tetramers and a fluorescent cell sorter, antigen-specific Tregs may be identified and sorted from the induction culture.

In a preferred embodiment, the CD4+CD25+ cells are selected with artificial MHC Class II/peptide tetramer complexes comprising a leucine zipper motif, a ligand with a polyvalent binding partner, and a fluorescent label as described in U.S. Application Publication No. 2003/0073102 A1. The method of producing such MHC/peptide tetramers in accordance with this embodiment of the method of the invention involves four basic steps: the expression of soluble monomeric MHC Class II molecules, peptide loading, multimerization, and fluorescent labeling, as briefly described below.

The soluble MHC Class II molecules DR, DQ, and DP, or subunits thereof chosen for use in the tetramer complex, will generally correspond to the MHC Class II genotype of the CD4+ T cells taken from the subject and/or the intended use of the Treg cells. However, in some cases it may be preferable to use an MHC Class II molecule that is not the MHC Class II type of the subject, such as if it is desired to produce Treg cells which are intended for use to prevent graft-versus-host disease, in which case the MHC Class II molecule chosen for use in the tetramer complex is the one expressed by the graft cells.

The soluble artificial MHC Class II molecules may be formed from separate soluble α and β chains that are produced from the extracellular domains with a linker region attaching a biotinylation site and a leucine zipper motif. The α subunits being, for example, HLA-DPα, HLA-DQα or HLA-DRα and the β subunits being, for example, HLA-DPβ, HLA-DQβ or HLA-DRβ. The structures are multimerized (e.g., tetramerized) via interaction with the polyvalent binding partner streptavidin. The binding partner can optionally be labeled with, for example, a radioactive molecule, a luminescent molecule, a fluorescent molecule, an enzyme, biotin and the like. The peptide is typically added to the secreted soluble molecules prior to multimerization.

The MHC Class II molecules, or subunits thereof, can be purified by methods known to the skilled artisan. Such methods include, for example, affinity purification (e.g., antibody, an epitope tag, and the like); column chromatography (e.g., HPLC, FPLC and the like) and other methods. For example, to purify DQ, DR and DP MHC Class II molecules, SPVL-3, L-243 and B7/27 columns, respectively, can be used (see, e.g., Ettinger et al., *J. Immunol.* 165:3232-38, 2000).

Preferably, the peptide is non-covalently bound to the MHC molecules in the tetramer complex, thereby allowing more flexibility in the use of multiple types of peptides per construct, and also multiple types of peptide per tetramer. Therefore, a single MHC molecule can be loaded with a large number of distinct peptides.

Figure 6:
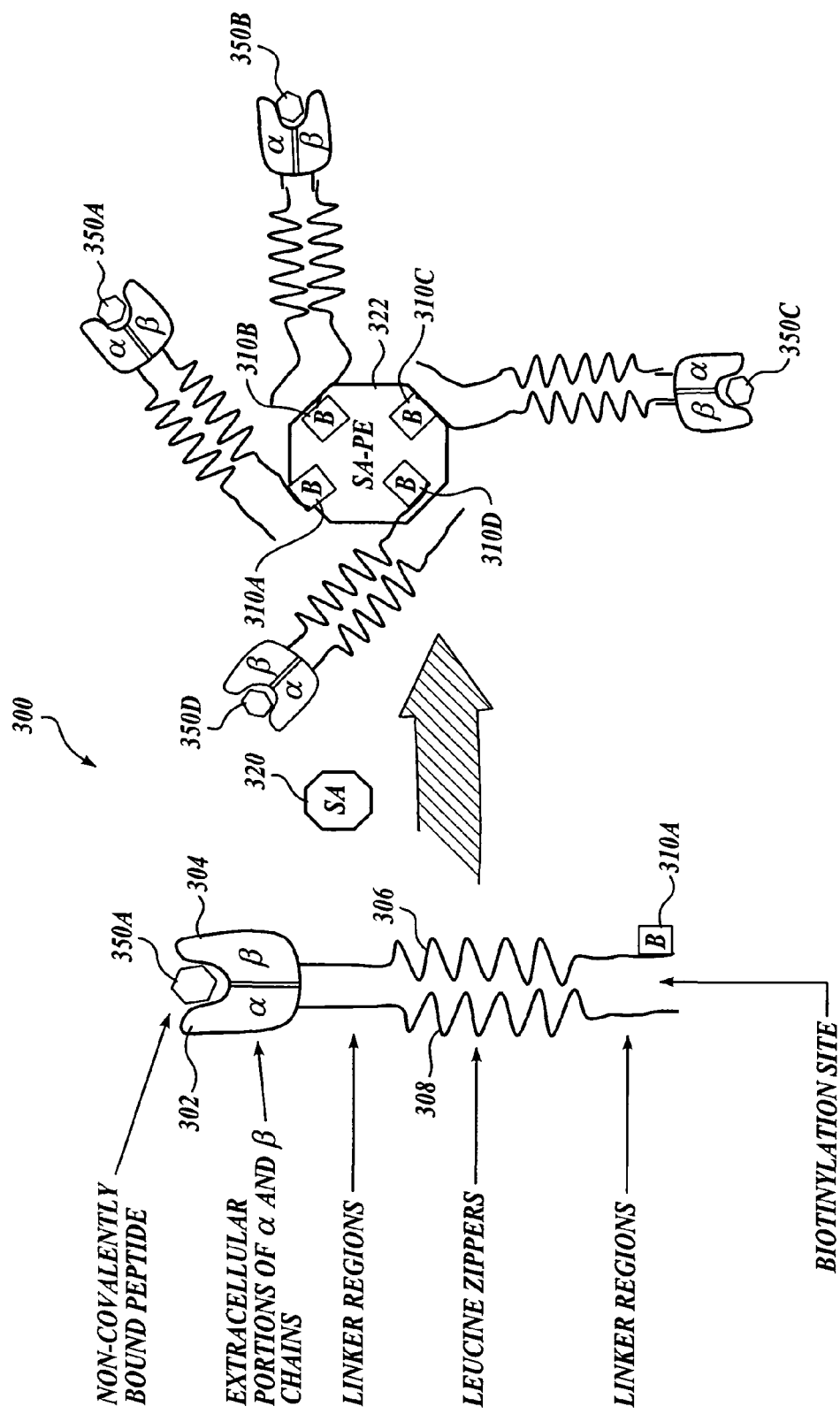
FIG. 6 is a schematic diagram illustrating an illustrative example of the type of MHC Class II/peptide complexes useful in one embodiment of the method of the present invention.

FIG. 6 illustrates an exemplary configuration of a HLA Class II tetramer 300 that is useful for selecting antigen-specific Treg in accordance with one embodiment of the method of the invention. As shown in FIG. 6, soluble recombinant Class II α chain portions 302, and β chain portions 304 are produced that incorporate a leucine zipper motif 306, 308 and a site for the enzymatic addition of biotin 310A. An exogenous peptide 350A is noncovalently attached in the peptide groove. Upon addition of streptavidin 320, a tetrameric complex is formed due to the four biotin binding sites 310A, 310B, 310C and 310D. Each of the four termini contains a Class II peptide interface suitable for binding to antigen-specific T cell receptors. Moreover, by using fluorophore-labeled streptavidin molecules, T cells that bind specific tetramers can be stained and sorted from those that do not bind, using flow cytometry.

A detailed description of an exemplary method of forming HLA-DRB*0401/peptide tetramers is described herein (see Example 4). While the description provided herein is in reference to HLA-DR, one of skill in the art will recognize that the described methods may also be applied to the DP and DQ MHC Class II molecules using routine methods known in the art of molecular biology. The methods of forming tetramers described herein in Example 4 and in U.S. Application Publication No. 2003/0073102 A1, can be adapted to form soluble tetramers for any desired HLA Class II molecule. The cDNA sequences of the various Class II HLA types are publically available from Genbank. Further, the use of HLA Class II tetramers as a tool for binding antigen-specific T cells in other contexts is known in the art and various artificial HLA Class II type tetramers have been described. For example, the use of HLA-DQ tetramers is described in Kwok et al., *J. Immunol.* 164:4244-4249, 2000. The use of HLA DRA1 0101/DRB 0401 tetramers is described in Novak et al., *J. Clin. Invest.* 104:63-67, 1999. The use of tetramers to identify antigen-specific T cells is also described in other references including, for example Holzer et al., *J. Allergy Clin. Immunol.* 110(2):199-208, 2002; Holzer et al., *J. Immunol.* 170:1218-1223, 2003; Danke et al., *J. Immunol.* 172:5967-5972, 2004; Reijonen et al., *Diabetes* 51:1375-1382, 2002; and Kwok et al., *J. Immunol. Methods* 268:71-81, 2002.

In another embodiment, the method of this aspect of the invention further comprises the step of expanding the ex vivo generated Treg cell population. In accordance with this embodiment, T cell expansion may be accomplished by culturing the antigen-specific CD4+CD25+Tmr+ Treg cells with a co-stimulatory agent comprising a CD3 activation and a CD28 activation for a time period sufficient to achieve the desired cell expansion. A number of anti-human CD3 monoclonal antibodies are commercially available, such as for example, OKT3, G19-4, Hit3a, and UCHT1 (Pharmigen, San Diego, Calif.). To further activate a population of T cells, a co-stimulatory or accessory molecule on the surface of the T cells, such as CD28, is stimulated with a ligand that binds to the accessory molecule. Accordingly, one of skill in the art will recognize that any agent capable of cross-linking the CD28 molecules can be used to stimulate T cells, such as for example, an anti-CD28 antibody or a natural ligand for CD28. Exemplary anti-CD28 antibodies or fragments thereof include monoclonal antibody 93 (IgG2; Bristol Myers Squibb, Princeton, N.J.), monoclonal antibody KOLT-2 (IgG1), and CD28.2 (Pharmigen, San Diego, Calif.). Exemplary natural ligands include the B7 family of proteins such as B7-1 (CD80) and B7-2 (CD86) (Freedman et al., *J. Immunol.* 137:3260-3267 (1987)). In a preferred embodiment, the molecule providing the activation signal, such as a CD3 ligand, and the co-stimulatory molecule, such as a CD28 ligand, are coupled to the same surface, such as a particle or bead. One, two, or more, stimulatory molecules may be attached to the same particle or bead. An exemplary method of T cell expansion according to this preferred embodiment is described in Example 8.

In one embodiment, the antigen-specific Tregs are expanded in the presence of an MHC/peptide complex in the form of a monomer or multimer. The MHC/peptide complex may be plate-bound or soluble.

The ex vivo generated Treg cells are expanded in culture for a time period ranging from about 10 days to about 14 days. Preferably, the expansion obtained is in the range of from about 10 fold to about 50 fold or higher. The expanded Treg population may be assayed for particular Treg characteristics, such as, for example, CD25 expression, antigen-specific suppressor activity, and FoxP3 expression, as described herein. In some embodiments, the expanded Treg cell population is re-selected with anti-CD25 and MHC Class II/peptide tetramers. In further embodiments, the method further comprises administering the expanded regulatory T cells to a subject in need thereof as described in more detail below.

The antigen-specific Treg cells obtained using the methods in accordance with this aspect of the invention preferably present all of the following characteristics: expression of the cell surface markers CD4+ and CD25+ (measured, for example, using anti-CD4 and anti-CD25 antibody reagents as described in Example 1); expression of FoxP3 (either protein expression as measured by a Western blot and/or FoxP3 mRNA transcription measured, for example, using the methods described in Example 1, or by flow cytometry, Roncador et al., *Eur. J. Immunol.* 35:1681-1691, 2005); IL-10 independent suppression (measured, for example, in a cytokine assay as described in Example 4); cell-to-cell contact dependent suppression of proliferation of autologous freshly isolated CD4+CD25− responder T cells which have been stimulated in culture, upon re-exposure to the cognate antigen used for induction (measured, for example, using a proliferation assay as described in Examples 1 and 2).

For the purposes of the present invention, an MHC Class II/peptide tetramer (Tmr+) enriched Treg population means at least 2% of the ex vivo generated and/or expanded CD4+CD25+ T regulatory population binds to the corresponding MHC Class II/peptide tetramer complex. In certain embodiments, a MHC Class II/peptide tetramer enriched Treg population means at least 5%, 10%, 12%, 15%, 18%, 20% and higher of the ex vivo generated and/or expanded Treg population binds to the corresponding MHC Class II/peptide tetramer complex and is CD4+CD25+. In further embodiments, after selection with MHC Class II/peptide tetramer containing the cognate antigen, at least 70% and higher, such as 80%, 90%, 95%, 99% to 100% of the selected Treg population binds to the corresponding MHC Class II/peptide tetramer complex and is CD4+CD25+.

In contrast to the ex vivo generated Treg cell populations generated by the methods of the present invention, circulating human peripheral blood typically contains between 4% and 10% CD4+CD25+ T cells, of which only about 1:20,000 to 1:200,000 CD4+CD25+ T cells are also Tmr+ for a particular antigen.

The present inventors have discovered that induction of human CD4+CD25+ T cells from CD4+CD25− cells correlates with increased expression of FoxP3 in the induced cells as further described in Examples 1, 3, 4, and 8, and described in Walker et al., *J. Clin. Invest.* 112:1437-1443, 2003, incorporated by reference herein. Therefore, FoxP3 expression is also a useful marker for verifying the presence and/or quantitating the number of Treg cells present in the isolated T cell population.

The antigen-specific Tmr+ regulatory T cells generated according to the method of the invention require re-exposure to the cognate antigen for activation and, once activated, these cells act to suppress the auto-reactive T cells as measured in an in vitro assay in a contact dependent manner, as demonstrated in Examples 4, 5 and 6. The present inventors have also discovered that once activated by cognate antigen, the Tmr+ regulatory T cells are also capable of suppressing the proliferation of responder T cells (also referred to as bystander suppression) in response to both cognate and non-cognate antigen as demonstrated in Examples 5 and 6. Therefore, the ex vivo generated regulatory T cells produced according to the method of the invention are advantageously immunologically specific at the site of inflammation and are not expected to cause generalized immunosuppression. Ligand-specific activation cell-to-cell contact dependence and bystander suppression are desirable properties for use in immunotherapy (Wang et al., *Immunity* 20:107-118, 2004; Levings et al., *J. Exp. Med* 196:1335-1346, 2002; Thornton et al., *J. Immunol.* 164:183-190, 2000).

The present inventors have discovered that the step of MHC/peptide selection of CD25+Tmr+ is effective to achieve this desired property of immunologic specificity. As shown in FIG. 8C and further described in Examples 5 and 6, a subset of CD25+Tmr− cells are also present in the induction culture, which exhibit non-specific suppression of responder T cells in response to any antigen stimulation. Therefore, in a preferred embodiment, the CD25+Tmr+ immunologically specific cells are purified away from the CD25+Tmr− non-specific cells through MHC/peptide selection prior to use as an immunotherapeutic agent.

The methods of generating human Treg cells described herein provide several unique advantages over other methods attempted in animal models. For example, due to the ability of these regulatory cells, once activated by their cognate antigen, to suppress bystander cells at the site of inflammation, the present methods provide the ability to generate Treg cells to any chosen antigenic peptide based on the subject's HLA haplotype, which is selected based on its specificity to the tissue for which tolerance is lost. Therefore, prior knowledge of a particular target antigen involved in the disease process of interest is not required. This is in contrast to systems that are limited by screening for the presence of low levels of naturally occurring antigen-specific Tregs based on a presumption that the Tregs are specific to an immunodominant epitope that is prevalent in the disease process. This advantage is especially important in the case of diseases with multiple epitopes or in which epitope spreading may occur during progression of the disease, such as is the case in type 1 diabetes (see, e.g., Kaufman et al., *Nature* 366:69-72, 1993). In addition, the present methods may be practiced using peripheral blood obtained at any period before or during an active disease process in contrast to other methods which require isolation of low frequency, naturally occurring antigen-specific Tregs that are likely to be at the site of disease and may not be found in circulation.

Pharmaceutical Compositions

In another aspect, the present invention provides a pharmaceutical composition comprising a T cell population containing antigen-specific CD4+CD25+ Treg cells in a formulation which is suitable for administration to a patient in need thereof. In some embodiments, the antigen-specific CD4+CD25+ Treg cells are specific for a self-antigen associated with an autoimmune or inflammatory disease. In one embodiment, the composition contains a mammalian CD4+CD25+ Treg cell population comprising a range of from about 2% to about 20% tetramer positive staining cells. The methods of generating antigen-specific CD4+CD25+ Treg cells described herein are useful for generating the T cell population for use in the composition according to this embodiment of the composition of the invention. In a preferred embodiment, the composition contains a mammalian CD4+CD25+ Treg cell population comprising greater than 70%, such as 80%, 90% up to 100% tetramer positive staining cells. The methods of generating and selecting antigen-specific CD4+CD25+ Treg cells described herein are useful for generating the cell populations in accordance with this preferred embodiment of the composition of the invention.

In some embodiments, the pharmaceutical compositions according to this aspect of the present invention comprise an enriched antigen specific Treg cell population in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans; mannitol; proteins; polypeptides or amino acids such as glycine; antioxidants; chelating agents such as EDTA; adjuvants and preservatives. Compositions of the present invention are preferably formulated for intravenous administration.

In some embodiments, the composition of the present invention contains a therapeutically effective amount of the CD4+CD25+ Treg cells in combination with an effective amount of another bioactive material.

The pharmaceutical composition comprising CD4+ CD25+ antigen-specific regulatory T cells is administered to a subject in need thereof in a manner appropriate to the disease to be treated and/or prevented. The quantity and frequency of administration will be determined by such factors as the condition of the patient and the type and/or severity of the patient's disease. Appropriate dosages may also be determined by clinical trials. An "effective amount" of the composition can be determined by a physician with consideration of individual differences in age, weight, disease severity, condition of the patient, route of administration and any other factors relevant to treatment of the patient. In general, a pharmaceutical composition comprising Treg cells may be administered at a dosage of about $10^5$ to $10^8$ cells/kg body weight, preferably $10^5$ to $10^6$ cells/kg body weight, including all integer values within these ranges. The compositions of the invention may also be administered multiple times at these dosages. The optimal dosage and treatment regime for a particular patient can readily be determined by one skilled in the art of medicine by monitoring the patient for signs of disease and adjusting the treatment accordingly.

The cells can be administered by using infusion techniques that are commonly used in immunotherapy, and may be administered to a patient subcutaneously, intradermally, intramuscularly, or by intravenous injection (see, e.g., Rosenburg et al., *New Eng. J. Med.*)

Methods of Treating and/or Preventing Autoimmune Diseases and Inflammatory Conditions In another aspect, the present invention provides methods for treating and/or preventing an autoimmune disease or inflammatory condition. The method according to this aspect of the invention comprises obtaining a sample containing T cells from a human subject in need thereof, determining the MHC Class II type of the subject, isolating a population of CD4+CD25− T cells from the sample, generating antigen-specific regulatory T cells by contacting the isolated CD4+ CD25− T cells in an induction culture with an induction agent for a sufficient period of time to generate antigen-specific CD4+CD25+ regulatory T cells; selecting the CD4+CD25+ antigen-specific regulatory T cell population by sorting the induction culture with a selection agent comprising at least one MHC Class II/peptide complex, expanding the CD4+ CD25+ regulatory T cell population and administering the expanded cell population to the subject.

The pathogenesis of a number of autoimmune diseases is believed to be caused by autoimmune T cell responses to self-antigens present in the organism. For example, autoreactive T cells have been implicated in the pathogenesis of multiple sclerosis (MS), rheumatoid arthritis (RA), type 1 diabetes (T1DM), and Pemphigus. The importance of Treg in the protection from autoimmunity has been demonstrated in various animal models. For example, depletion of CD4+CD25+ Treg from mice produces a spectrum of spontaneous organ-specific autoimmune manifestations and increases the susceptibility to induction of autoimmune diseases such as collagen-induced arthritis (Sakaguchi et al., *J. Exp. Med.* 161: 72-87, 1985; Morgan et al., *Arthritis Rheum.* 48:1452-1460, 2003). Moreover, studies have demonstrated that autoimmune diseases can be ameliorated by the addition of Treg. It has been shown that Treg therapy can effectively delay and cure mice in a variety of mouse models of immunological diseases including diabetes, colitis, gastritis and graft-versus-host disease (Salomon et al., *Immunity*, 12:431-440, 2000; Read et al., *J. Exp. Med.*, 192:295-302, 2000; Taylor et al., *Blood* 99:3493-3499, 2002; Hoffman et al., *J. Exp. Med* 196: 389-399, 2002; and Edinger et al., *Nat. Med.* 9:1144-1150, 2003). In addition, treatment of mice with anti-CD3 antibodies has been shown to induce regulatory T cells, which prevents diabetes (Kohm et al., *J. Immunol.* 174:4525-4534, 2005; Belghith et al., *Nat. Med.* 9:1202-1208, 2003).

In humans, the ability of Treg to regulate T cells in an antigen-specific manner has been demonstrated in the context of various diseases, including regulation of T cells specific to tumor antigens (Viguier et al., *J. Immunol.* 173:1444-1453, 2004); alloantigens in the setting of bone marrow transplantation (Ng et al., *Blood* 98:2736-2744, 2001); and the foreign antigen HA as described herein (Walker et al., *PNAS* 102: 4103-4108, 2005).

Therefore, immunotherapy with Treg cells obtained from T cells of a human subject is useful in the context of a cellular therapy for regulating the immune response in the subject. For example, the Treg cells may be used for preventing and/or treating a disease or condition such as an autoimmune disease, inflammatory disease, or in the treatment and/or prevention of transplant rejection and also to prevent graft-versus-host reactions.

Antigenic peptides useful in the methods of the invention may be identified by eluting peptides from MHC molecules known to be associated with autoimmunity, for example the HLA-DQ and DR molecules that confer susceptibility to several common autoimmune diseases such as type 1 diabetes, rheumatoid arthritis and multiple sclerosis. Antigenic peptides useful in the present invention also include synthesized peptides predicted to bind to MHC molecules associated with autoimmune diseases. TABLE 3 provides an exemplary list of suitable antigenic peptides for use in the methods herein and for producing the pharmaceutical compositions of the present invention. Antigenic peptides may be also be identified for a selected polypeptide antigen using the methods described in U.S. patent application Ser. No. 10/116,846, incorporated by reference herein.

Method of Treating and/or Preventing Type 1 Diabetes:

Type 1 diabetes (T1DM) is an autoimmune disease mediated by the destruction of islet cells, the insulin-producing β-cells of the pancreas. This destruction represents a loss of immune tolerance and is due to pathogenic CD4+ and CD8+ T and B cell responses directed against proteins found in the islet. In the NOD mouse model, studies have demonstrated the ability to use islet specific Treg to protect and treat diabetes in several animal models (Tang et al., *J. Exp. Med* 199: 1455-1465, 2004; Tarbell et al., *J. Exp. Med.*, 199:1467-1477, 2004).

In humans, several studies have identified abnormalities in the number or function of CD4+CD25+ Treg in patients with T1DM (Kukreja et al., *J. Exp. Med.* 199:1285-1291, 2004; Kriegel et al., *J. Exp. Med.* 199:1285-1291, 2004). A lack of Treg is also implicated in the pathogenesis of diabetes by the finding of diabetes in both animals depleted of Treg and in humans with IPEX (see Wildin et al., *Nat. Genet.* 27:18-20, 2001). Accordingly, the method of the invention may be used to generate antigen-specific Treg cells for use in treating and/or preventing type 1 diabetes in those at risk for diabetes. In particular, those at risk for developing diabetes include first degree relatives, and especially those individuals that have antibodies to islet-specific antigens. The methods of the invention can therefore be used to treat patients with active disease as well as prophylaxis for those identified (based on genetic or antibody screening) as being at risk for developing type 1 diabetes.

The MHC Class II molecules HLA-DQ8 and HLA-DQ-2, DRB 1*0401, 0404 and DRB1*0301 confer the highest risk for individuals that have, or are at risk for type 1 diabetes.

Illustrative examples of useful antigens and peptides thereof for various autoimmune diseases are described in more detail below and are shown in TABLE 2 and TABLE 3 below.

Many islet-specific T cell auto-antigens have been identified that contribute to diabetes disease development (see, Masteller et al., *J. Immunol.* 171:5587-5595, 2003; Reijonen et al., *Diabetes* 51:1375-1382, 2002; Eisenbarth et al., *Nat. Immunol.* 3:344-345, 2002; and Maus et al., *Clin. Immunol.* 106:16-22, 2003), including glutamic acid decarboxylase 65 (GAD65), insulin, and IA2 as shown in TABLE 2 and TABLE 3.

Studies have shown that 70-80% of type 1 diabetic patients have auto-antibodies against the antigen glutamic acid decarboxylase 65 (GAD65) (Reijonen et al., *Diabetes* 51:1375-1382, 2002). Antibodies against GAD65 can be identified prior to, and at the time of, disease onset, using HLA Class II tetramers (as described in more detail below), implicating GAD specific autoimmunity in the development of T1DM (Reijonen et al.). The present inventors have generated GAD65 specific CD4+CD25+ Tregs from subjects diagnosed with type 1 diabetes using the methods described herein, as described in more detail below (see FIG. 9 and Example 6). Accordingly, in one aspect, the invention provides a method for preventing and/or treating type 1 diabetes in a subject in need thereof, comprising administering to the patient an amount of islet-specific Treg cells according to the methods described herein effective to treat and/or prevent the disease in the subject.

Method of Treating and/or Preventing Graft Versus Host Disease

The major problem in hematopoietic stem cell transplantation is graft-versus-host disease (GVHD), which is caused by alloreactive T cells present in the infused hematopoietic stem cell preparation. Studies in mice have demonstrated that adoptive transfer of Treg can block graft-versus-host disease without affecting the graft-versus-leukemia response (Edinger et al., *Nat. Med.* 9:1144-1150, 2003).

Accordingly, in one aspect, the invention provides a method for reducing the risk of, or the severity of, an adverse GVHD effect in a patient who is undergoing a hematopoietic stem cell transplant, comprising administering to the patient an amount of regulatory T cells specific for mismatched antigens between the recipient and donor according to the methods described herein effective to reduce the risk or severity of an adverse GVHD effect in the patient.

Method of Treating and/or Preventing an Inflammatory Condition Associated with Organ Transplantation:

Graft rejection mediated by alloreactive host T cells is a major problem which is treated by long-term immunosuppression of the transplant recipient. Accordingly, in one embodiment, the invention provides a method of reducing the risk of, or the severity of, an adverse immune response in a patient that has undergone, is undergoing, or will undergo, an organ transplant, comprising administering to the patient an amount of a population of transplant-specific Treg cells according to the methods described herein effective to reduce the risk or severity of an adverse immune response in the patient.

The transplant-specific Treg cells may be generated using the methods described herein. For example, in one embodiment, the method comprises obtaining a sample containing T cells from the patient and determining the MHC Class II of the patient. A population of CD4+CD25− T cells is isolated from the sample and transplant-specific regulatory T cells are produced by contacting the isolated T cells in a culture vessel with an induction agent. In some embodiments, the induction agent comprises at least one antigenic peptide specific to the transplant organ or tissue and a population of antigen presenting cells that are MHC Class II matched to the patient. The cells in the induction culture are sorted with at least one MHC Class II/peptide complex, wherein the peptide is cognate with the induction agent. In some embodiments, the sorted cells are then expanded in a culture vessel, and administered in an amount effective to reduce the risk and/or the severity of an adverse immune response in the patient.

The methods described in this aspect of the invention are useful for reducing the risk of, or the severity of, any adverse immune response in a transplant recipient, such as graft-versus-host disease. The methods may be applied to solid organ (e.g., kidney(s), heart, lung(s), liver and pancreas) transplant recipients or to allogeneic bone marrow or autoimmune patients with autologous or allogeneic bone marrow. A reduction of severity of an adverse immune response may be measured by any suitable method. Nonlimiting examples include the reduction or elimination of acute graft rejection, the reduction or elimination of chronic rejection, the reduction or elimination of graft-versus-host disease, and/or the reduction or elimination of the need for high doses of immunosuppressive drugs.

Method of Treating and/or Preventing Multiple Sclerosis:

The pathogenesis of autoreactive T cells in MS is believed to arise from T cell responses to myelin antigens and in particular to myelin basic protein (MBP). Although MBP-reactive T cells can be isolated from both healthy individuals and MS patients, the T cells isolated from MS patients are found to undergo in vivo activation and occur at higher precursor frequency in blood and cerebrospinal fluid in MS patients. These MBP reactive T cells produce TH1 cytokines including IL-2, TNFα and γ-interferon which facilitate migration of inflammatory cells into the central nervous system and exacerbate myelin-destructive inflammatory responses in MS.

In animal models, myelin reactive T cells have been shown to be involved in the pathogenesis of experimental autoimmune encephalomyelitis (EAE), which resembles MS. EAE is induced in susceptible animals by injecting myelin-reactive T cell lines. When activated in vitro, very small numbers of myelin-reactive T cells are required to induce EAE. EAE has been shown to be prevented by depleting the myelin-reactive T cells (Lohse et al., *Science*, 244:820-822, 1989). Based on the results in experimental models such as EAE, it is believed that depletion of autoreactive T cells may improve the clinical course of MS, as well as other autoimmune diseases.

In humans, T cell vaccines have been used in clinical trials to attempt to deplete self-reactive T cells. The antigen targeted has been MBP, and more particularly the amino acid region that comprises residues 13-33 or 87-99 or 139-154 of MBP as shown in TABLE 3. Other MS autoantigens have been described, including proteolipid protein (PLP) and myelin oligodendrocyte glycoprotein (MOG) and peptides derived therefrom, as further described in TABLE 2 and TABLE 3.

Accordingly, in one embodiment, the invention provides a method of treating and/or preventing multiple sclerosis in a subject in need thereof, comprising administering to the subject an amount of a population of Tregs specific to at least one self-antigen associated with multiple sclerosis according to the methods described herein effective to treat and/or prevent multiple sclerosis in the subject.

TABLE 1

HLA CLASS II ASSOCIATED AUTOIMMUNE DISEASES

| AUTOIMMUNE DISEASE | ASSOCIATED HLA ALLELE |
|---|---|
| Addison's Disease | DRB1*0404 |
| Autoimmune Hepatitis in Brazil and Argentina | DRB1*1302 |
| Autoimmune Hepatitis in Caucasian | DRB1*0301*0401 |
| Autoimmune Hypothyroidism | DRB1*0301 |
| Celiac Disease | DQB1*0201, DQB1*0302 |
| Chronic Beryllium Syndrome | DPB1*0201 |
| Chronic Lyme Arthritis | DRB1*4 and DRB1*1501 |
| Familial Dilated Cardiomyopathy | DRB1*4 |
| Goodpasture's Syndrome | DRB1*15 |
| Graves Disease | DRB1*0301 |
| Insulin Autoimmune Syndrome | DRB1*0406 |
| IDDM in Caucasian (Influenced by associated DR allele) | DQB1*0302, DQB1*0201 |
| IDDM in Japan | DRB1*0405-DQB1*0401 DRB1*0901-DQB1*0303 |
| Juvenile Dermatomyositis | DQA1*0501 |
| Lambert-Eaton Myasthenia Gravis | DRB1*0301-DQB1*0201 |
| Multiple Sclerosis | DRB1*4, DRB1*3, DRB1*1501 |
| Myasthenia Gravis | DRB1*0301 |
| Pauciarticular Juvenile RA | DRB1*0801, DRB1*11 |
| Pemphigus Foliaceous | DRB1*0404, DRB1*14 |
| Pemphigus Vulgaris in Asia | DRB1*14-DQB1*0503 |
| Pemphigus Vulgaris | DRB1*0402 |
| Rheumatoid Arthritis in American Indian | DRB1*1402 |
| Rheumatoid Arthritis in Caucasian | DRB1*0404DRB1*0101, DRB1*0401 |
| Rheumatoid Arthritis in Japan | DRB1*0405 |
| Relapsing Polychondritis | DRB1*4 |
| Scleroderma | DRB1*11 |
| Sjogren's Syndrome | DRB1*0301-DQB1*0201 |

Gebe et al., Tissue Antigens 59(2): 78-87, 2002.

TABLE 2

EXEMPLARY ANTIGENIC PROTEINS ASSOCIATED WITH AUTOIMMUNE DISEASES

| DISEASE | HLA TYPE | ANTIGEN | REFERENCE |
|---|---|---|---|
| Type 1 Diabetes (T1DM) | DRB1*0301, DRB1*0401 DRB1*0404 DQB1*0302 | insulin, IA-2, glutamic acid decarboxylase (GAD65), Islet-Specific Glucose-6-Phosphatase Catalytic Subunit-Related Protein (IGRP) and heat shock protein 60 (hsp-60). | Masteller et al., J. Immunol. 171: 5587-5595, 2003; Reijonen et al., Diabetes 51: 1375-1382, 2002; Eisenbarth et al., Nat. Immunol. 3: 344-345, 2002; and Maus et al., Clin. Immunol. 106: 16-22, 2003. |
| Pemphigus Folacius | DRB1*14, DRB1*0404 | desmoglein-1 | Lombardi et al., "Common human leukocyte antigen alleles in pemphigus vulgaris and pemphigus foliaceus Italian patients," J. Invest. Dermatol. 113: 107-10, 1999. |
| Pemphigus Vulgaris (PV) | DRB1*0402, DRB1*1401 | desmoglein-3 | Amagai, "Autoantibodies against cell adhesion molecules in pemphigus," J. Dermatol. 21: 833-7, 1994. |
| Multiple sclerosis | DRB1*1501, DRB5*0101 DQB1*0602 DRB1*0401 DRB1*0404 DRB1*1303, DRB1*0301 | protein components in the myelin sheath, including Myelin Basic Protein (MBP), myelin oligodendrocyte glycoprotein (MOG) and proteolipid protein (PLP) | Oksenberg et al., "Multiple sclerosis: genomic rewards." J. Neuroimmunol. 113: 171-84, 2001. |
| Celiac Disease | DQA1*0501/ DQB1*0201 and DQA1*0301/ DQB1*0302 | gliadin and glutenin protein families | Sjostrom et al., "Identification of a gliadin T-cell epitope in coeliac disease: general importance of gliadin deamidation for intestinal T-cell recognition," Scand. J. Immunol, 1998. |
| Rheumatoid Arthritis | DRB1*0401 DRB1*0404 DRB1*0101 | Type II collagen Filaggrin, vimentin, Aggrecan G1, Gp39 | Verheijden et al., human cartilage glycoprotein-39 as a candidate autoantigen in rheumatoid arthritis. Arthritis Rheum. 40: 1115-1125, 1997. Hill et al., "Cutting edge: the conversion of arginine to citrulline allows for a high-affinity peptide interaction with the rheumatoid arthritis-associated HLA-DRB1*0401 MHC class II molecule." J. Immunol. 171: 538-541, 2003. |
| myasthenia gravis (MG) | DRB1*0301 | acetylcholine receptor | |
| Hashimoto's thyroiditis | | Thyroid peroxidase, thyroglobulin | |

TABLE 2-continued

EXEMPLARY ANTIGENIC PROTEINS ASSOCIATED WITH AUTOIMMUNE DISEASES

| DISEASE | HLA TYPE | ANTIGEN | REFERENCE |
|---|---|---|---|
| Scleroderma | DRB1*11<br>DRB1*05<br>DRB1*15 | Topoisomerase | Kuwana M, Arthritis and Rheumatism 44: 1654-1659, 2001. |
| Graves' disease | DRB1*0301 | Thyrotropin receptor | |

TABLE 3

EXEMPLARY ANTIGENIC PEPTIDES USEFUL TO GENERATE TREGS

| Antigen | Peptide | MHC Class II restriction | Peptide sequence | SEQ ID NO: |
|---|---|---|---|---|
| Pro-Insulin | B24-C36 | DR3 | FFYTPMSRREVED | SEQ ID NO: 1 |
| Insulin | B9-23 | DQ8 DR4 | SHLVEALYLVCGERG, | SEQ ID NO: 2 |
| Insulin | A5-16 | DQ8 DR4 | QCCTSICSLYQL | SEQ ID NO: 3 |
| GAD65 | 555-567 | DRB1*0401,0404, DRB4*DRB1*0401,0404 | NFFRMVISNPAAT | SEQ ID NO: 4 |
| GAD65 | 274-286 | DRB1*0401,0404, DRB4*DRB1*0401,0404 | IAFTSEHSHIFSLK | SEQ ID NO: 5 |
| IGRP | 13-24 | DRB1*0401 | QHLQKDYRAYTF | SEQ ID NO: 6 |
| IGRP | 123-145 | DQ8 | WYVMVTAALSYTISRMEESSVTL | SEQ ID NO: 7 |
| IGRP | 195-214 | DQ8 | HTPGVHMASLSVYLKTNVFL | SEQ ID NO: 8 |
| IGRP | 277-294 | DQ8 DR4 | MFLRSCQGENGTKPSFRL | SEQ ID NO: 9 |
| IA-2 | 335-352 | DR4 | TAGYFVYGAFDPLLAVAD | SEQ ID NO: 10 |
| IA-2 | 601-618 | DQ8 DR4 | RQHARQQDKERLAALGPE | SEQ ID NO: 11 |
| IA-2 | 709-736 | DR4 | LAKEWQALCAYQAEPNTCATAQ GEGNIK | SEQ ID NO: 12 |
| IA-2 | 752-775 | DR4 | KLKVESSPSRSDYINASPIIEHDP | SEQ ID NO: 13 |
| IA-2 | 805-815 | DQ8 DR4 | VIVMLTPLVED | SEQ ID NO: 14 |
| IA-2 | 853-872 | DR4 | SFYLKNVQTQETRTLTQFHF | SEQ ID NO: 15 |
| MBP | 13-33 | DR1501, DR1 | SKYLATASTMDHARHGFLPR | SEQ ID NO: 16 |
| MBP | 87-99 | DR1501, DR1 | VVHFFKNIVTPRTPPPSQGK | SEQ ID NO: 17 |
| MBP | 139-154 | DR1501, DR1 | AHKGFKGVDAQTLSK | SEQ ID NO: 18 |
| PLP | 40-60 | DRB1*1501, DR3, DRB1*0401 | TGTEKLIETYFSKNYQDYEYL | SEQ ID NO: 19 |
| PLP | 95-116 | DRB1*1501, DR3, DRB1*0401 | GFYTTGAYRQIFGDYLTT | SEQ ID NO: 20 |
| PLP | 175-192 | DRB1*1501, DR3, DRB1*0401 | HCLGKWLGHPDKF | SEQ ID NO: 21 |
| MOG | 35-55 | DRB1*1501, DRB1*0401 | EVGWYRPPFSRVVHLYRNGK | SEQ ID NO: 22 |
| MOG | 97-108 | DRB1*1501, DRB1*0401 | TCFFRDHSYQEEA | SEQ ID NO: 23 |
| MOG | 183-191 | DRB1*1501, DRB1*0401 | FVIVPVLGP | SEQ ID NO: 24 |
| Collagen | 1068-1080 | DRB1*0401, DRB1*0101, DRB1*0405 | AGIAGFKGEQGPKG | SEQ ID NO: 25 |
| Collagen | 261-273 | DRB1*0401, DRB1*0101, DRB1*0405 | GGVGPIGPPGERGA | SEQ ID NO: 26 |

TABLE 3-continued

EXEMPLARY ANTIGENIC PEPTIDES USEFUL TO GENERATE TREGS

| Antigen | Peptide | MHC Class II restriction | Peptide sequence | SEQ ID NO: |
| --- | --- | --- | --- | --- |
| Collagen | 429-442 | DRB1*0401, DRB1*0101, DRB1*0405 | SGFQGLPGPPGPPGEGGGK | SEQ ID NO: 27 |
| Collagen | 593-610 | DRB1*0401, DRB1*0101, DRB1*0405 | RGFTGLQGLPGPPGPSGD | SEQ ID NO: 28 |
| Vimentin | 65-77 | DRB1*0401 | SAVRARSSVPGVR | SEQ ID NO: 29 |
| Gp39 | 263-275 | DRB1*0401 | RSFTLASSETGVG | SEQ ID NO: 30 |
| Aggrecan G1 | 280-292 | DRB1*0401 | AGWLADRSVRYP | SEQ ID NO: 31 |
| Gliadin | 56-88 | DQA1*0501/DQB1*0201, DQ8 | LQLQPFPQPQLPYPQPQLPYPQPQLPYPQPQPF | SEQ ID NO: 32 |
| Gliadin | 138-152 | DQA1*0501/DQB1*0201, DQ8 | PEQPQQSFPEQERP | SEQ ID NO: 33 |
| Gliadin | 206-217 | DQA1*0501/DQB1*0201, DQ8 | SGQGSFQPSQQN | SEQ ID NO: 34 |
| Glutenin | 707-742 | DQ8 | SGQGQRPGQWLQPGQGQQGYYPTSPQQSGQGQQLGQ | SEQ ID NO: 35 |
| Desmoglein-3 | 78-94 | DRB1*0402 | QATQKITYRJSGVGIDQ, | SEQ ID NO: 36 |
| Desmoglein-3 | 96-112 | DRB1*0402 | PFGIFVVDKNTGDLNIT | SEQ ID NO: 37 |
| Desmoglein-3 | 189-205 | DRB1*0402 | HLNSKIAFKJVSQEPAG | SEQ ID NO: 38 |
| Desmoglein-3 | 205-221 | DRB1*0402 | GTPMFLLSRNTGEVRTL | SEQ ID NO: 39 |
| Desmoglein-3 | 250-266 | DRB1*0402 | QCECNIKVKDVNDNFPM | SEQ ID NO: 40 |
| Desmoglein-3 | 342-358 | DRB1*0402 | SVKLSIAVKNKAEFHQS | SEQ ID NO: 41 |
| Desmoglein-3 | 376-392 | DRB1*0402 | NVREGIAFRPASKTFTV | SEQ ID NO: 42 |
| Desmoglein-1 | 1-22 | DRB1*14, DRB1*0404 | EWIKFAACREGEDNSKRNP | SEQ ID NO: 43 |
| Acetylcholine receptor | 320-337 | DR3, DQ8 | IPNIMFFSTMKRPSREKQ | SEQ ID NO: 44 |
| Thyrotropin receptor | 158-176 | DRB1*0301 | ITDNPYMTSIPVNAFQGLC | SEQ ID NO: 45 |
| Thyrotropin receptor | 207-222 | DRB1*0301 | LNKNKYLTVIDKDAFG | SEQ ID NO: 46 |
| Thyrotropin receptor | 237-252 | DRB1*0301 | SVTALPSKGLEHLKEL | SEQ ID NO: 47 |
| Thyrotropin receptor | 248-263 | DRB1*0301 | HLKELLARNTWTLKKL | SEQ ID NO: 48 |
| Thyrotropin receptor | 343-362 | DRB1*0301 | FQDTHNNAHYYVFFEEQEDE | SEQ ID NO: 49 |
| Thyrotropin receptor | 357-376 | DRB1*0301 | EEQEDEIIGFGQELKNPQEE | SEQ ID NO: 50 |
| Topoisomerase | 276-386 | DRB1*11, DRB1*15, DRB1*05 | RIMPEDIIINC | SEQ ID NO: 51 |

The following examples merely illustrate the best mode now contemplated for practicing the invention, but should not be construed to limit the invention. All literature citations are expressly incorporated by reference.

EXAMPLE 1

This example describes a method of generating CD4+ CD25+ T regulatory cells from peripheral CD4+ cells with the inducing agents anti-CD3/anti-CD28. The diagram shown in FIG. 1 illustrates the steps included in the method described in this example.

Isolation of CD4+CD25− T Cells from PBMC:

To isolate CD4+CD25− T cells, human peripheral blood was obtained from normal healthy donors, and peripheral blood mononuclear cells "PBMCS" were prepared as described in Walker et al., *J. Clin. Invest.*, 112:1437-1443, 2003. Briefly, the PBMCs were isolated by centrifugation over Ficoll-Hypaque gradients. CD4+ T cells were purified by depletion of cells expressing CD8, CD11b, CD16, CD19, CD36, and CD56 with the CD4+ No-touch T cell isolation kit (Miltenyi Biotec, Auburn, Calif.). CD4+CD25− cells were isolated by negative selection with CD25 microbeads (Miltenyi Biotec, Auburn, Calif.). Purity was determined to be greater than 99% CD25− by FACS analysis (data not shown).

In order to rule out the possibility that the less than 1% of residual naturally isolated CD25+ are capable of expanding in the induction culture, CD25+ cells from the FACS sort were tested by activating them and culturing for 10 days. It was found that less than 1% of these cells remained alive by day 10 (data not shown), thereby demonstrating that residual naturally isolated CD25+ T cells are not capable of expanding in the induction cultures.

Generation of CD4+CD25+ Treg Cells by Induction with Anti-CD3/ANT1-CD28:

CD4+CD25− cells were isolated from PBMC as described above and were then cultured either in the presence of 5 μg/ml plate-bound anti-CD3 (UCHT1, Pharmigen, San Diego, Calif.) and 1 μg/ml soluble anti-CD28 (CD28.2; Pharmigen). The cells were removed from the plate-bound anti-CD3 antibody after 24 hours. The expression of CD4+ and CD25+ was monitored by FACS analysis over a 14 day period and the results are shown in FIG. 2B. As shown in FIG. 2B, the percentage of CD4+CD25+ cells peaked at about 75% to 80% during the time period from day 3 to day 10. After 10 days of culture, the CD4+CD25+ cells were stained with antibodies to CD4 and CD25 and FACS sorted into CD25+ and CD25− subgroups. The CD4+CD25− and CD4+CD25+ populations were clearly delineated by FACS analysis.

Assay of Ex Vivo Generated CD4+CD25+ Treg Function

Generation of antigen presenting accessory cells (APCs): Accessory cells were obtained by isolating the positive fraction of the CD4+ No-touch magnetic sort after depleting CD8+ T cells with CD8 microbeads (Miltenyi Biotec, Auburn, Calif.). Accessory cells were irradiated with 5,000 rads prior to addition to the induction cultures.

Cell proliferation assay: Ex vivo generated CD4+CD25+ Treg, freshly isolated CD4+CD25− T responder cells, and a mixture of the two populations were plated at $2.5 \times 10^3$ cell population per well. The two cell populations were co-cultured a 1:1 ratio ($2.5 \times 10^3$ per well, each cell population). Each cell population was cultured with irradiated T cell depleted accessory cells (APCs) at $2.5 \times 10^4$ per well. The cells were cultured with 5 μg/ml soluble anti-CD3 (UCHT1; Pharmigen, San Diego, Calif.) and 2.5 μg/ml soluble anti-CD28 (CD28.2; Pharmigen). Proliferation was measured by 3H-thymidine incorporation. During the final 16 hours of a 5-6 day assay, $^3$H-thymidine was added and proliferation was measured by scintillation counting.

Cell proliferation assessed by CFSE Dilution: CD4+ CD25+ regulatory T cells were generated by induction with plate-bound CD3 plus soluble anti-CD28 overnight and the cells were cultured for 9 additional days. On day 10 the cells were sorted for CD4+CD25+ cells. The CD4+CD25+cells were then labeled with carboxyfluoroscein succinimidyl ester, "CFSE" which is cleaved by non-specific esterases after entering a cell and thereafter remains in the cytoplasm of the cell for days to months. If the cells are undergoing division, the amount of CFSE present in each daughter cell after a division is half that of the parent. The CD4+CD25+ CFSE labeled cells were then cultured with or without CFSE labeled and biotinylated responder CD25− cells in the presence or absence of a transwell separating the cell populations. The CD4+CD25+ and CD25− Responder ("R") cells were cultured at a 1:1 ratio and stimulated with soluble anti-CD3/anti-CD28. The CD25+ T regulatory cells and CD25− T responder cells were analyzed separately for CFSE dilution on day 6 (as shown in FIGS. 2E-2G) and day 9 (as shown in FIGS. 2H-2J) of co-culture.

Results: The results of the functional assays on the ex vivo generated CD4+CD25+ cells are shown in FIGS. 2A, 2D and 2E-2J. The ex vivo generated CD4+CD25+ Treg cells are designated as CD25+ cells, and the CD4+CD25− freshly isolated responder cells are also designated as "R".

Figure 2A:
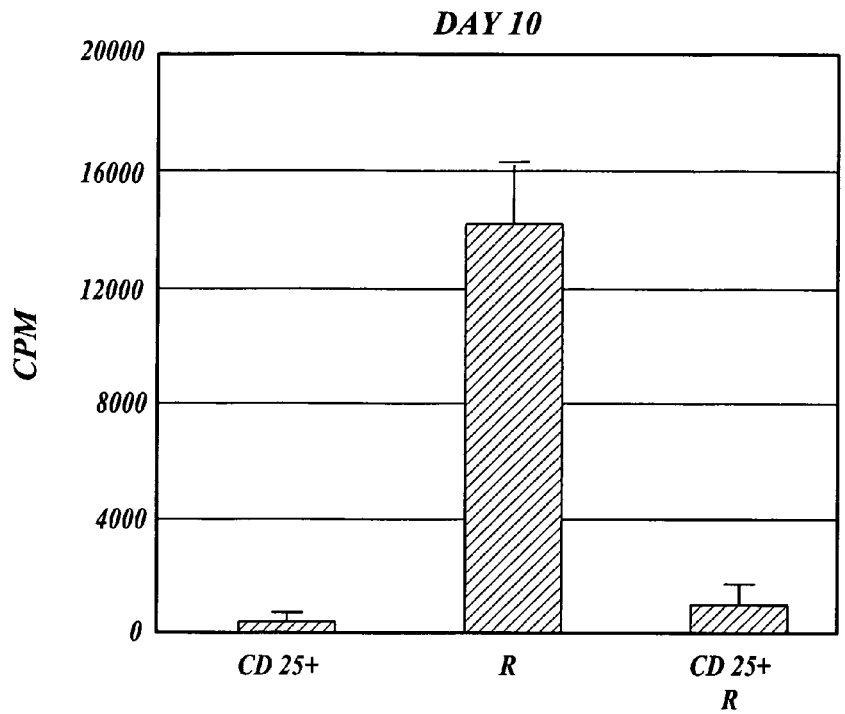
FIG. 2A presents graphical results demonstrating that CD4+CD25+ regulatory T cells induced with plate-bound anti-CD3 and soluble anti-CD28 suppress the proliferation of freshly isolated CD4+CD25− responder ("R") T cells, as described in Example 1.
Figure 2B:
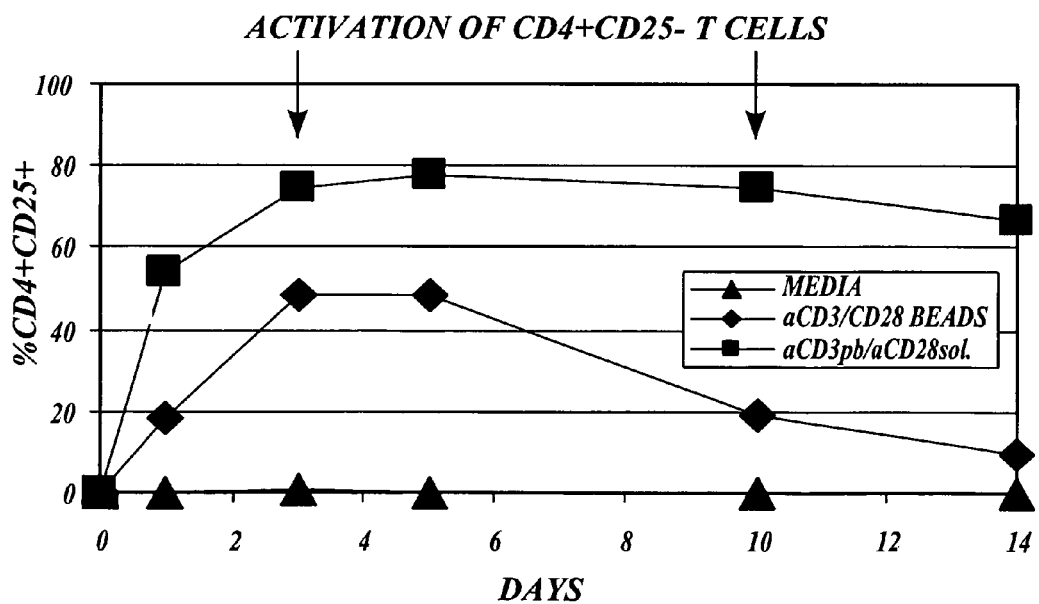
FIG. 2B presents results showing the percentage of CD4+CD25+ regulatory T cells produced as a function of the length of time of induction with anti-CD3/anti-CD28, as described in Example 1.
Figure 2C:
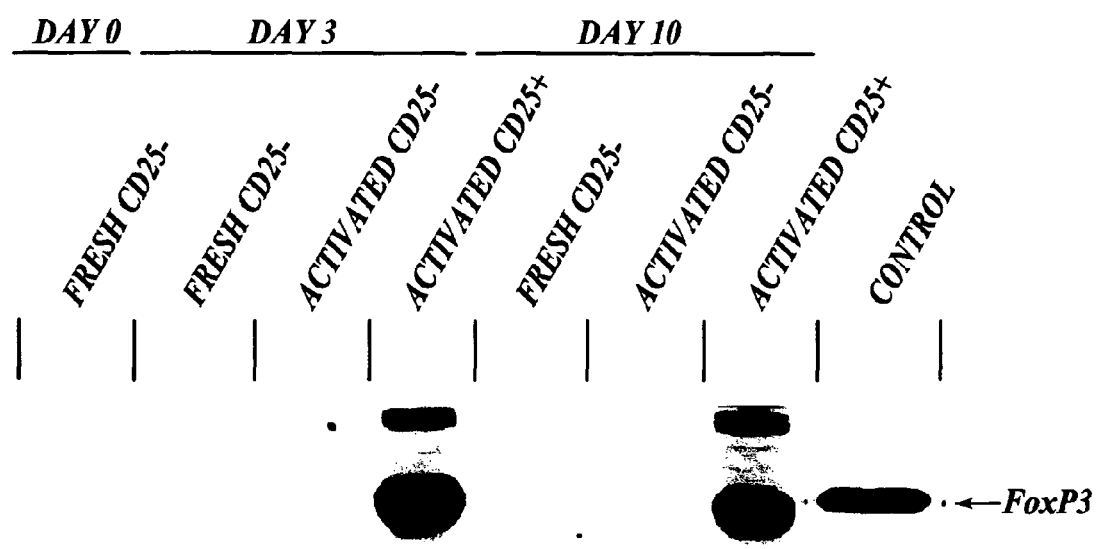
FIG. 2C presents a Western blot demonstrating that CD4+CD25+ regulatory T cells express FoxP3 protein, whereas CD4+CD25− T cells do not express FoxP3, as described in Example 1.

As shown in FIG. 2A, the ex vivo produced CD25+ cells did not proliferate in the cell proliferation assay (e.g., they are anergic). In contrast, the freshly isolated CD4+CD25− "R" T cells did proliferate in response to anti-CD3 and anti-CD28 as expected. In the mixed culture, the ex vivo generated CD25+ Treg cells suppressed the proliferation of the CD25− T responder cells stimulated with anti-CD3 and anti-CD28. These data are from one experiment which is representative of eight separate experiments with an observed suppression range of from about 60-95%.

Figure 2D:
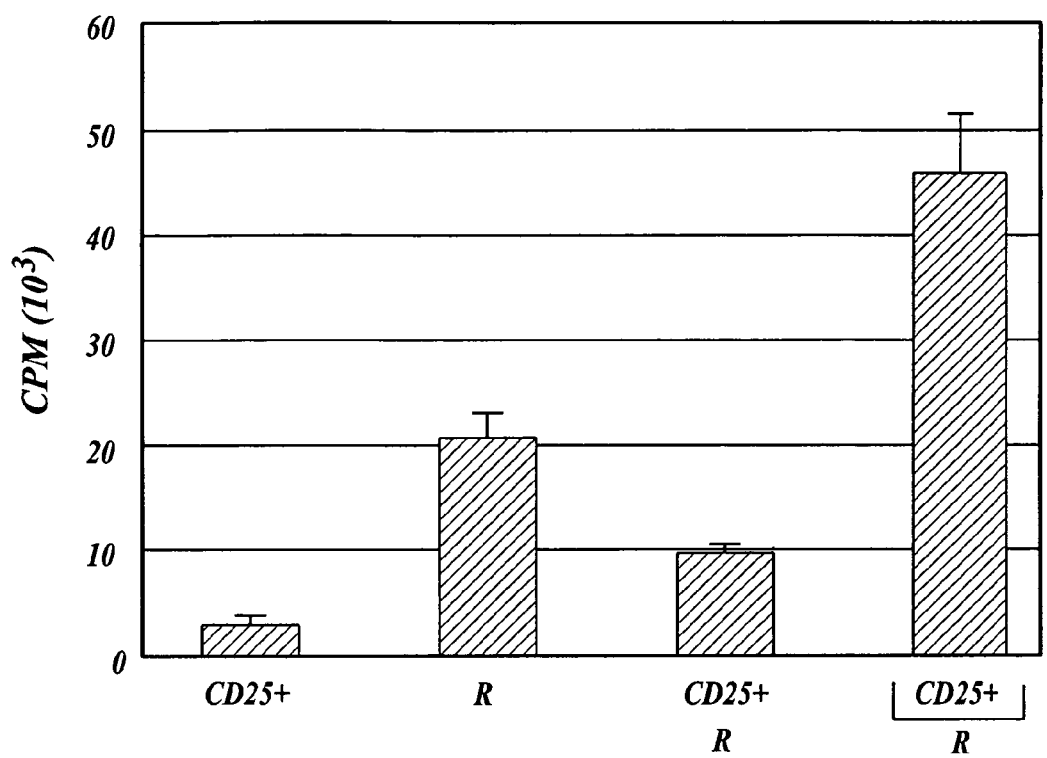
FIG. 2D presents graphical results demonstrating that suppression of proliferation of CD4+CD25− responder cells ("R") by anti-CD3 induced regulatory T cells is cell contact dependent, as described in Example 1.
Figure 2E:
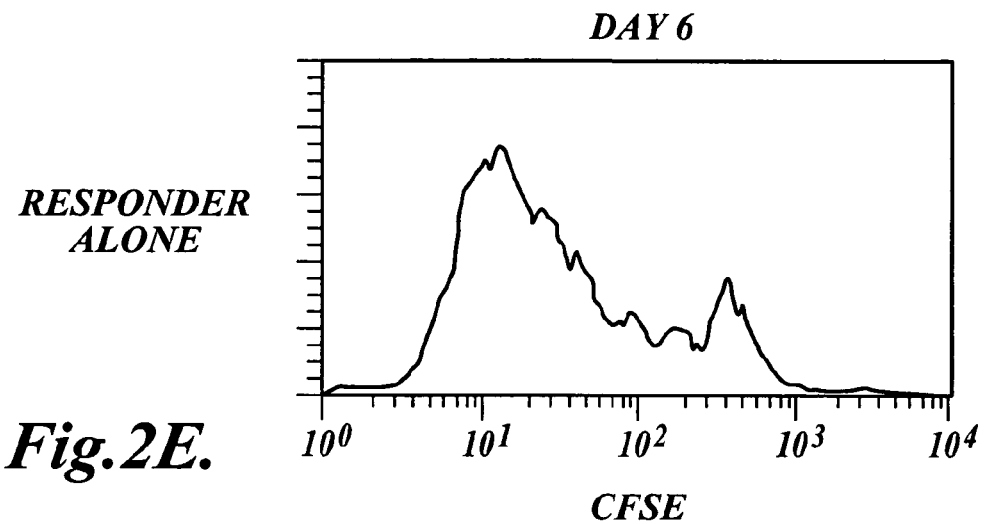
FIG. 2E to FIG. 2J present graphical results demonstrating suppression of proliferation of CD4+CD25− responder cells by ex vivo produced regulatory T cells using CFSE dye labeled cells. Normal proliferation of CD4+CD25− responder cells is shown at day 6 (FIG. 2E) and day 9 (FIG. 2H). Suppression of CD4+CD25− responder cells by co-cultivation with CD4+CD25+regulatory T cells is shown at day 6 (FIG. 2F) and day 9 (FIG. 2I). The addition of a transwell between the cell populations eliminates suppression of the CD4+CD25− responder cells at day 6 (FIG. 2G) and day 9 (FIG. 2J)
Figure 2F:
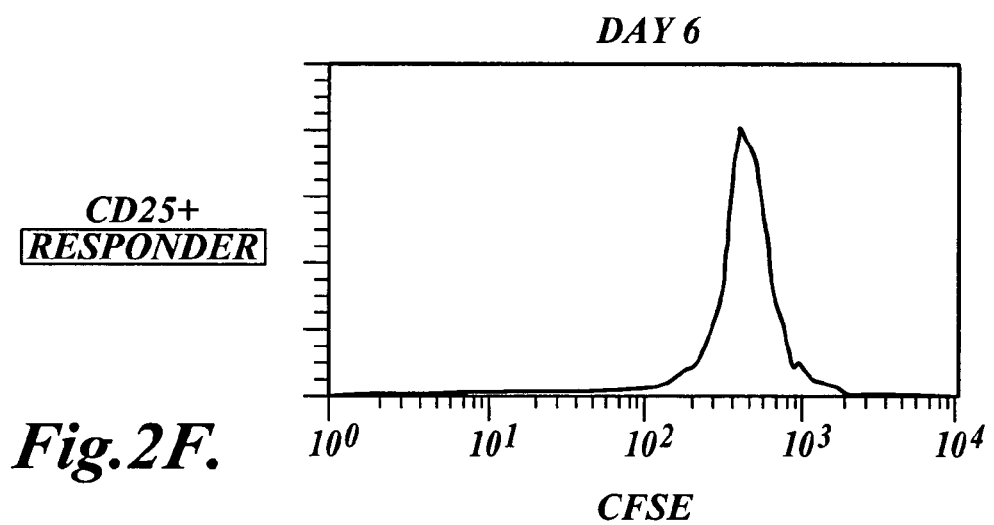
Figure 2G:
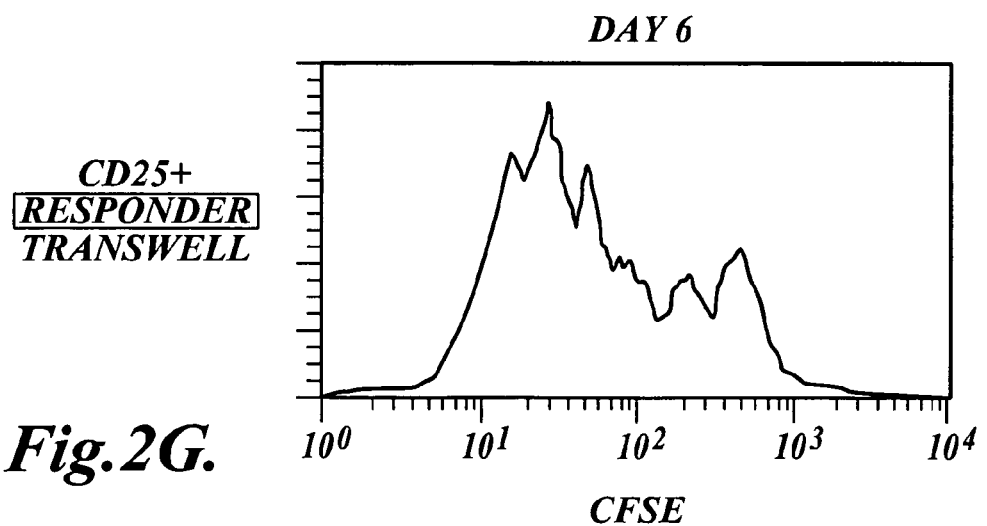
Figure 2H:
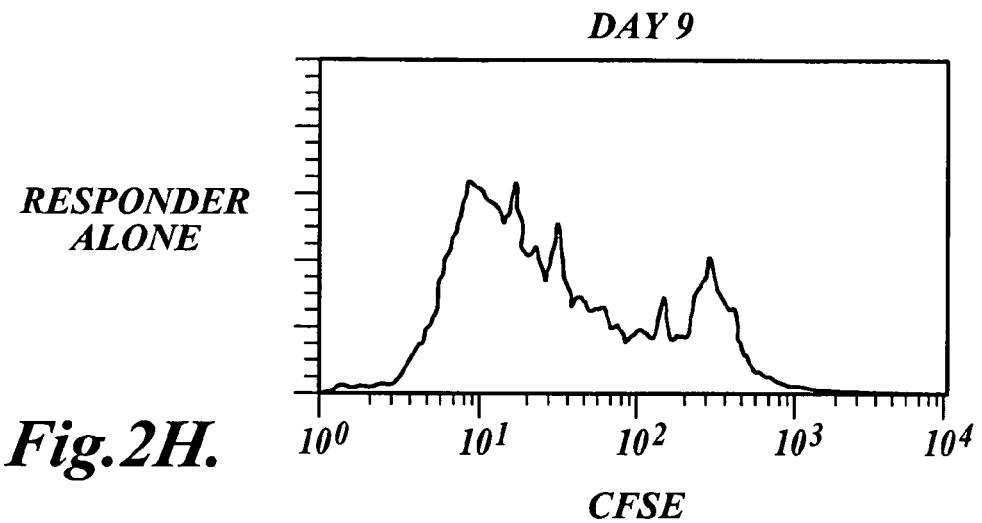
Figure 2I:
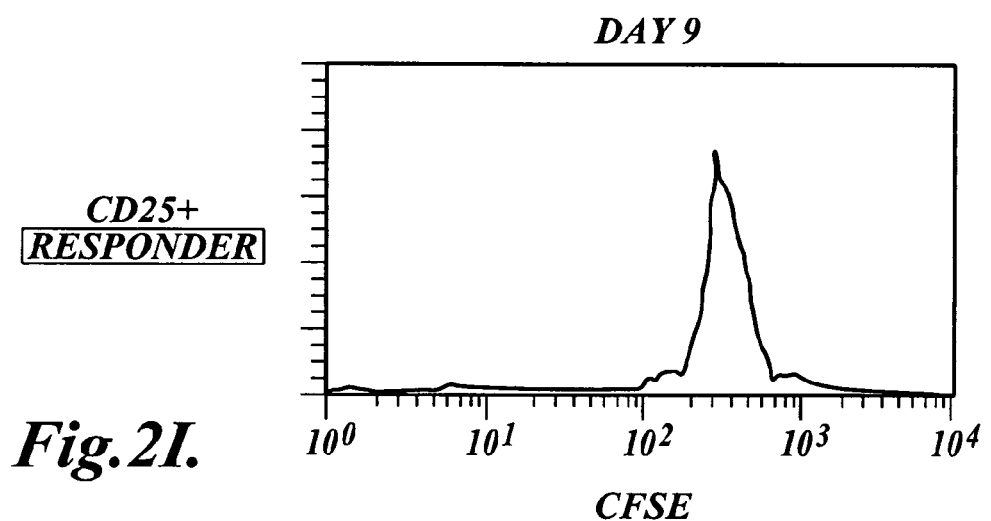
Figure 2J:
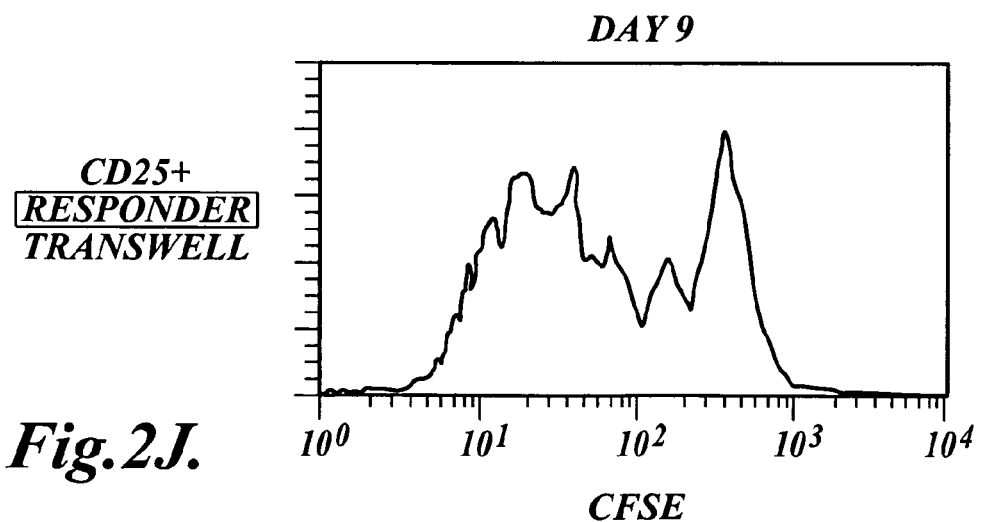

As shown in FIG. 2D, the suppressive activity of ex vivo generated CD4+CD25+ T regulatory cells requires cell to cell contact. As shown, in the mixed culture the ex vivo generated CD25+ Treg cells suppressed the proliferation of the CD25-T responder cells stimulated with anti-CD3 and anti-CD28, consistent with the results shown in FIG. 2A. In contrast, when the CD25+ and R cell populations were separated by a transwell, as indicated by the brackets around the CD25+ cells, proliferation of the R cells was not suppressed.

As described above, the CFSE dye was used to determine the extent of proliferation in individual cell types in mixed cultures (CFSE labeled cells become successively dimmer with each cell division). As shown in FIG. 2E and FIG. 2H, responder CD4+CD25− cells alone proliferate through several rounds of cell division. In contrast, responder cells do not proliferate when co-cultured with CD4+CD25+ ex vivo produced regulatory T cells (CD4+CD25+), as shown in FIG. 2F (day 6), and FIG. 2I (day 9). This suppressive effect is eliminated in the presence of a transwell separating the two cell populations, as shown in FIG. 2G (day 6), and FIG. 2J (day 9). Thus, the ex vivo generated regulatory T cells suppress T responder cell proliferation in a cell to cell contact dependent manner.

Analysis of FoxP3 Expression:

Western Blot Analysis: Isolated CD25+ and CD25− T cell populations from day 3 and day 10 of the induction culture shown in FIG. 2A and described above were washed in PBS and lysed and sonicated in lysis buffer (25 mM Tris pH 8.5, 2% lithium dodeccyl sulfate, 1 mM EDTA, 10 mM sodium fluoride, 1 mM sodium orthovanadate, 1× Roche Complete protease inhibitors) and protein levels were quantified (using a BCA assay; Pierce). Lysates were separated on 4-12% gradient bis-Tris gels (Invitrogen) and transferred to nitrocellulose membranes. Membranes were blocked for 3 hours in TBS/0.1% Tween-20 with 5% nonfat dry milk, probed with polyclonal rabbit-anti-FoxP3 antiserum (1:2000) overnight at 4° C. in the same buffer and developed using standard protocols. Western blots were stripped and re-probed with TFIIB (Santa Cruz) for a loading control. For a positive control, 293T cells were transfected with a human FoxP3 cDNA clone.

Results: The Western blot analysis of CD25+ and CD25− sorted samples taken from the induction culture is shown in FIG. 2C. As shown, the CD25+ Treg cells expressed high levels of FoxP3 protein at the time points sampled (day 3 and day 10). In contrast, no FoxP3 protein expression was detected in freshly isolated CD4+CD25− responder T cells or in CD4+CD25− cells isolated from the induction culture.

Quantitative FoxP3 PCR Assay

For quantitative real-time PCR (QPCR) analysis, RNA was extracted using an RNeasy Mini Kit (Qiagen, Valencia, Calif.) according to the manufacturer's instructions, and cDNA was prepared with 2.5 µM random hexamers (Applied Biosystems Inc., Foster City, Calif.). Message levels were quantified by real-time PCR using the ABI 7000 Sequence Detection System (Applied Biosystems Inc.). Amplification was carried out in a total volume of 25 µl for 40 to 50 cycles of 15 seconds at 95° C., 1 minute at 60° C., and product was detected using SYBR Green I dye (Molecular Probes Inc., Eugene, Oreg.). Samples were run in triplicate, and their relative expression was determined by normalizing expression of each target to GAPDH, and then comparing this normalized value to the normalized expression in a reference sample to calculate a fold-change value. Primers were designed so that amplicons spanned intron/exon boundaries to minimize amplification of genomic DNA.

Primer sequences were as follows:

```
GAPDH:
5'-CCACATCGCTCAGACACCAT-3'            (SEQ ID NO: 52)
and

5'-GGCAACAATATCCACTTTACCAGAGT-3';     (SEQ ID NO: 53)

FoxP3:
5'-GAAACAGCACATTCCCAGAGTTC-3'         (SEQ ID NO: 54)
and

5'-ATGGCCCAGCGGATGAG-3'               (SEQ ID NO: 55)
```

Results: FoxP3 transcript was detected in the ex vivo generated CD25+ Treg cells. No FoxP3 expression was detected in the freshly isolated CD4+CD25− responder T cells or in the CD4+CD25− cells derived from the induction culture, in concurrence with the Western blot data (FIG. 2C) (data not shown).

EXAMPLE 2

This example demonstrates that CD4+CD25+ Regulatory T cells can be generated from cell populations enriched for memory cells and naïve cells derived from peripheral CD4+ T cells.

Preparation of Cell Populations Enriched for Naïve and Memory Peripheral T Cells:

CD4+ T cells from peripheral blood were obtained as described in Example 1. The memory T cell population having the markers CD4+CD25−CD45RA−CD45RO+ was sorted by FACS into a memory cell enriched pool and the naïve T cell population having the markers CD4+CD25−CD45RA+CD45RO− was sorted by FACS into a naïve cell enriched pool.

Generation of CD4+CD25+ Regulatory T Cells:

The memory T cell pool and the naïve T cell pool were each induced with plate-bound anti-CD3 and soluble anti-CD28 for 10 days as described in Example 1. After 10 days in culture, the cells were stained with antibodies to CD4 and CD25 and FACS sorted into CD25+ and CD25− subgroups.

Functional Assays: After 10 days in culture, the cells in each induction culture were FACS sorted on the basis of CD4+ and CD25+ expression. The sorted cell populations were assayed for the ability to suppress the proliferation of freshly isolated CD4+CD25− T responder cells in a proliferation assay as described in Example 1. In addition, cell contact dependent suppression was assayed by culturing the sorted cell populations in 24-well plates at 50,000 cells/well either in the presence or absence of a 4 µM trans-well separating the CD4+CD25+ cells from CD4+CD25− cells.

Figure 3A:
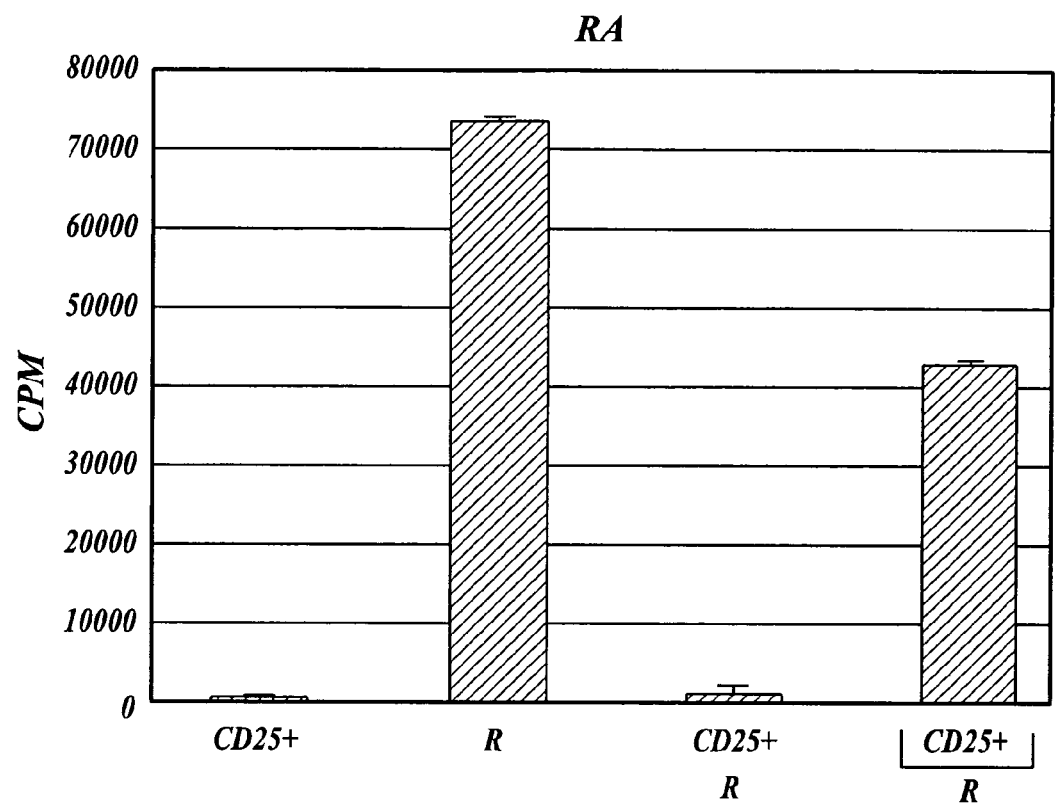
FIG. 3A presents graphical results demonstrating that CD4+CD25+ regulatory T cells are generated from a peripheral CD4+CD25− RA+ (naïve) T cell population using the methods provided in accordance with one embodiment of the present invention, as described in Example 2.
Figure 3B:
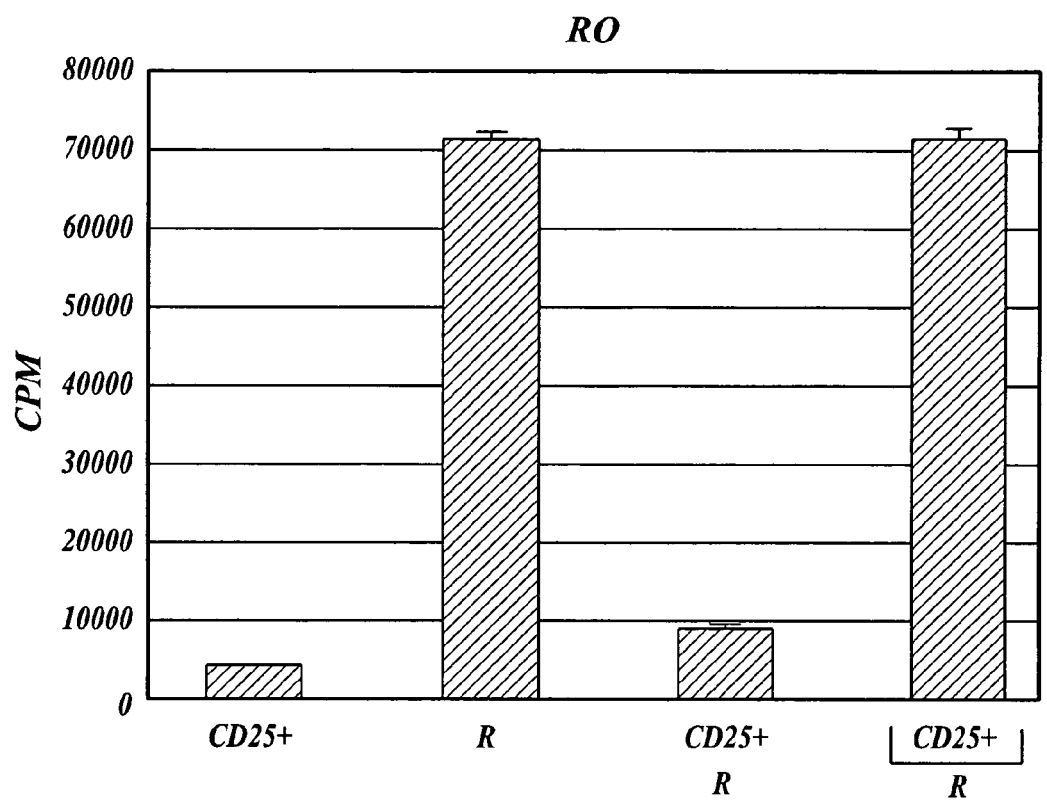
FIG. 3B presents graphical results demonstrating that CD4+CD25+ regulatory T cells are generated from a peripheral CD4+CD25− RO+ (memory) T cell population using the methods provided in accordance with one embodiment of the present invention, as described in Example 2.

Results: The induction cultures derived from the CD45+RO+ (memory) and the CD45+RA+ (naïve) T cells each resulted in ex vivo generated CD25+ cells (40% and 50% respectively). The proliferation assay results of the Treg generated from the RA+ naïve cell population is shown in FIG. 3A. The proliferation assay results of the Treg generated from the RO+ memory cell population is shown in FIG. 3B. As shown, the ex vivo generated CD4+CD25+ Treg cells (shown in bold) from both naïve and memory cell populations were capable of suppressing the freshly isolated CD25-T responder cells in a cell contact dependent manner (transwell cultures are shown in brackets). These results demonstrate that T regulatory cells can be generated from both naïve and memory T cell pools. In addition, the ex vivo generated Treg cells suppress T responder cell proliferation in a cell-to-cell contact dependent manner.

EXAMPLE 3

This example demonstrates that allo-reactive CD4+CD25+ regulatory T cells are induced by culturing with allogeneic dendritic cells.

Derivation and Culture of Mature Dendritic Cells:

PBMC were prepared by centrifugation over Ficoll-Hypaque gradients as described in Example 1. Cells were plated for adherence for 2 hours and then washed of nonadherent cells. Cells were then cultured with 1000 U/ml GM-CSF and 50 ng/ml IL-4 (R&D systems). After 6-9 days, 2 ng/ml IL-1β (R&D systems) and 1 µg/ml PGE$_2$ (Calbiochem), TNFalpha, and IL-6 were added to the culture for 2-3 days. Mature dendritic cells were then harvested, irradiated (5000 rads) and used to stimulate CD4+CD25− T cells in the assay described below.

Generation of CD4+CD25+ Regulatory T Cells:

CD4+CD25− cells were isolated from PBMC as in Example 1. The CD4+CD25− cells were placed in culture and induced with allogeneic dendritic cells using a 1:50 ratio of CD25− T cells to allogeneic dendritic cells. After 10 days in culture, the cells were stained with antibodies to CD4 and CD25 and FACS sorted into CD25+ and CD25− subgroups.

Functional Assay: The CD4+CD25+ Treg cells induced with allo-antigen were analyzed in a proliferation assay for the ability to suppress freshly isolated CD4+CD25− autologous responder T cells. The proliferation assay included the ex vivo generated CD4+CD25+ Treg cells induced with allogenic dendritic cells, CD4+CD25− freshly isolated autologous responder T cells, and a culture of the two cell populations (1:1 ratio) with or without a trans-well separating the populations, each plated at 25,000 cells/well. The cell populations were each activated with allogeneic dendritic cells at a ratio of 1:25-50 T responder CD25− T cells to allogeneic dendritic cells. Cell proliferation was measured as described in Example 1.

Figure 4A:
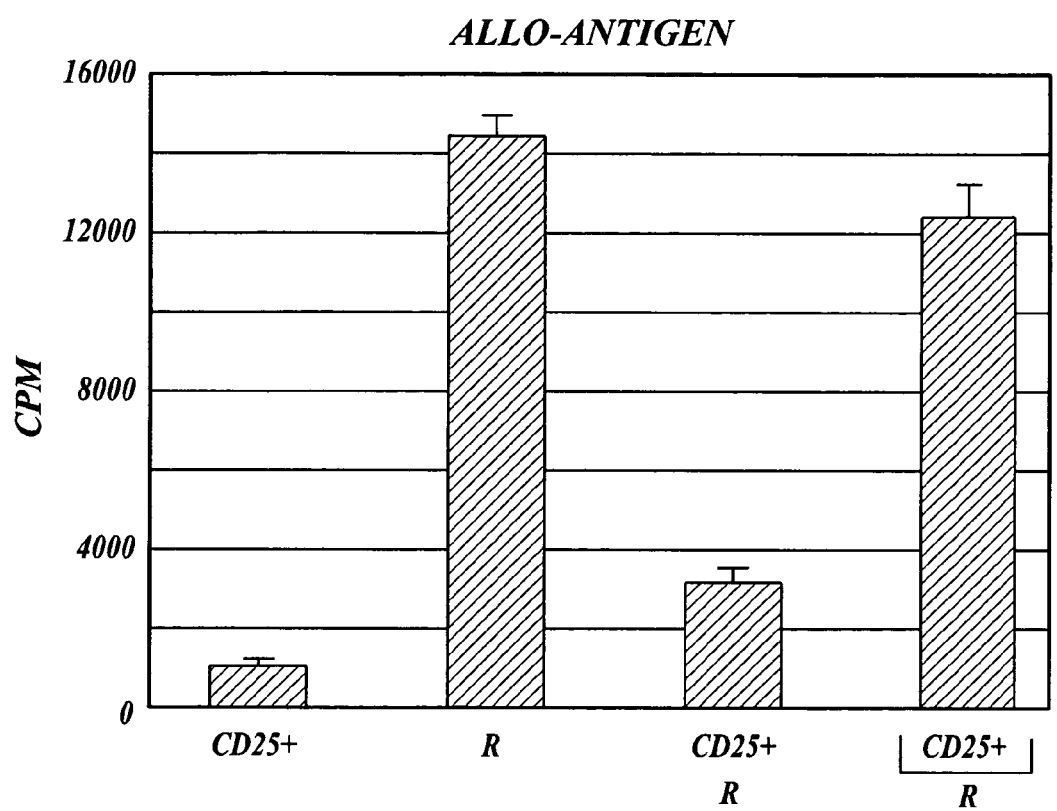
FIG. 4A presents graphical results demonstrating that CD4+CD25+ regulatory T cells are generated from peripheral CD4+CD25− T cells upon induction with allogeneic dendritic cells, as described in Example 3.

Results: The results shown in FIG. 4A are presented as the means of triplicates from one experiment with error bars representing standard deviations, and are representative of three experiments. As shown in FIG. 4A, the allo-induced CD4+CD25+ Treg cells did not proliferate in the presence of the allo-antigen. The freshly isolated CD25− cells did proliferate in response to allo-antigen, as expected. Suppression of proliferation was the suppression was abrogated when the cell populations were separated by a trans-well (shown by the brackets).

Figure 4B:
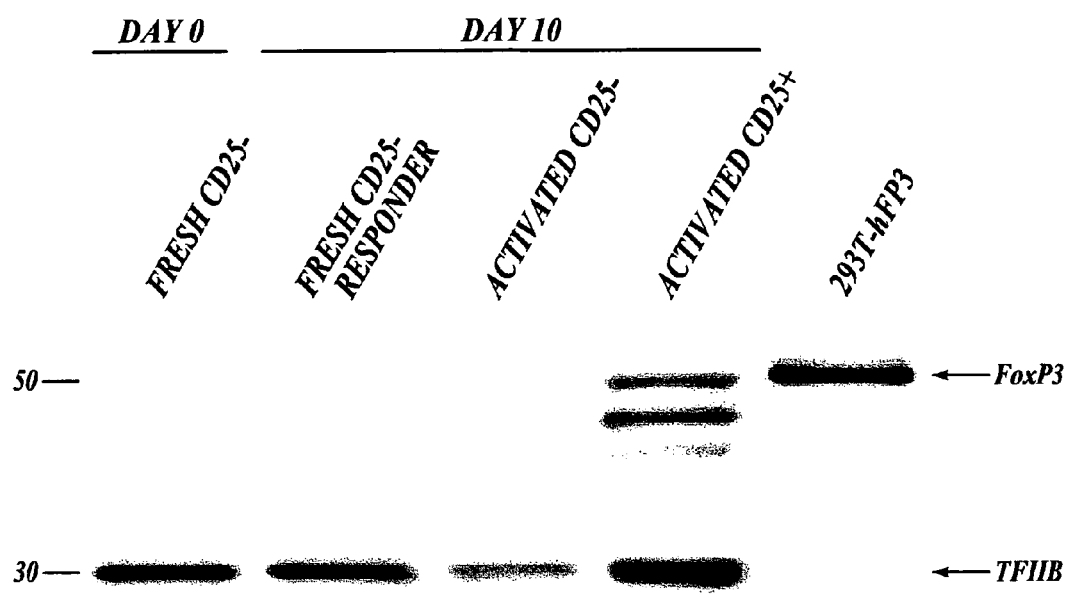
FIG. 4B presents a Western blot demonstrating that FoxP3 protein expression correlates with the ex vivo generated regulatory T cell population shown in FIG. 4A, as described in Example 3.

FIG. 4B shows Western blot analysis of FoxP3 expression. FoxP3 expression is observed in the allo-antigen induced CD25+ ex vivo generated Treg cells. No expression is detected in freshly isolated CD25− cells or CD4+CD25− cells sorted after induction with the allo-antigen. 293T cells transfected with a hFoxP3 cDNA clone were included as a positive control. Furthermore, blockade of IL-10 or TGF-β did not alter the ability of the ex vivo generated CD4+CD25+ cells to suppress proliferation (data not shown).

Discussion: This data demonstrates that allo-antigen-specific Treg cells that are contact dependent, cytokine independent, and express FoxP3 can be generated by activation of CD4+CD25− T cells with allogeneic dendritic cells. Such Treg cells are derived from T cells naïve to the allo-antigen. Because the allogeneic DC were the only antigen presenting cells in the cultures, it is likely that the ex vivo generated Treg were specific for allo-antigens. This observation is consistent with studies that have identified naturally occurring Treg specific to allo-antigens in animal models of bone marrow transplant and in human bone marrow recipients.

EXAMPLE 4

This example demonstrates that antigen-specific CD4+ CD25+ regulatory T cells are generated by induction with the foreign antigen, hemagluttanin (HA) and that the antigen-specific population can be selected with an MHC Class II/cognate peptide complex.

Figure 5:
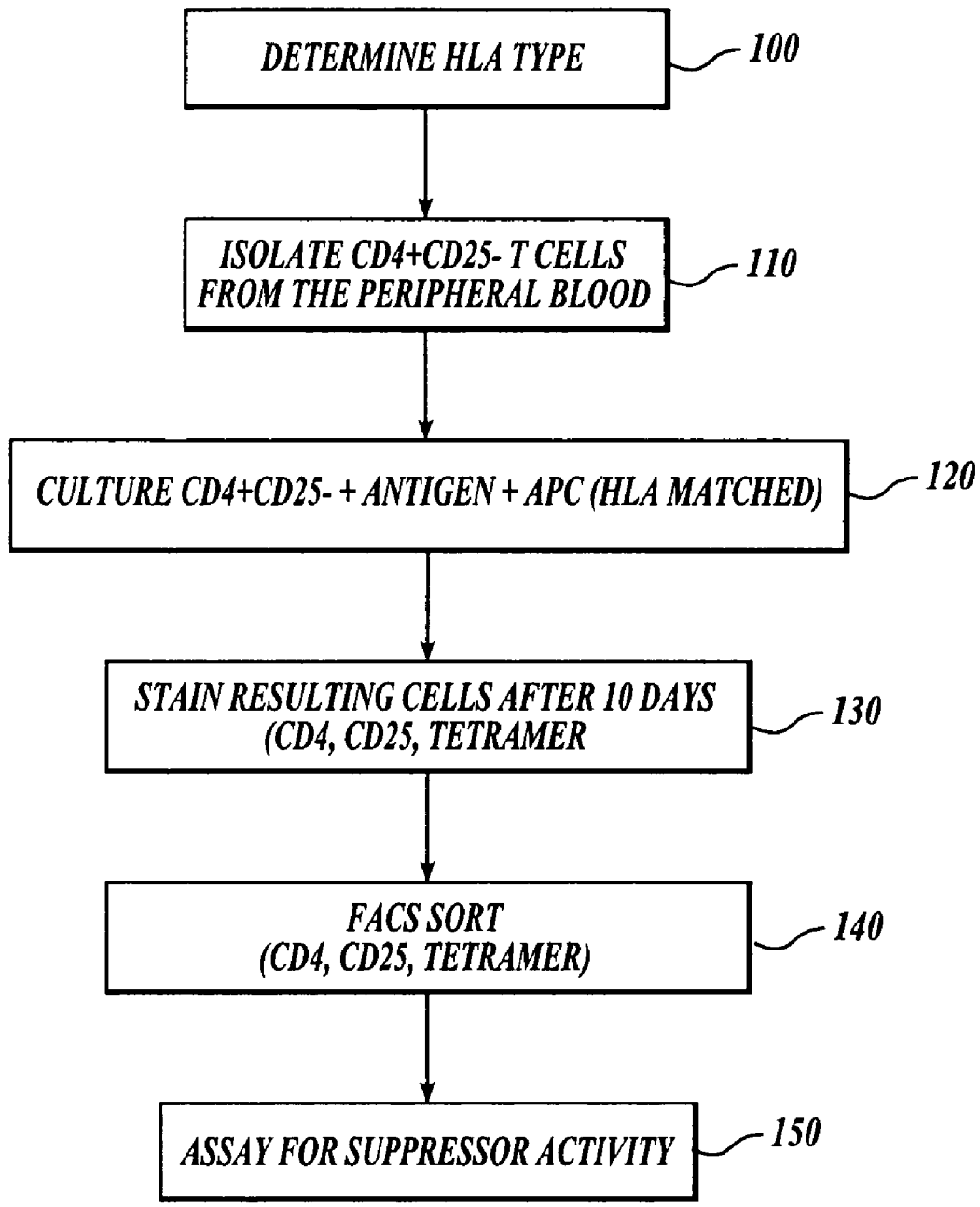
FIG. 5 is a flow diagram illustrating a method of generating antigen-specific CD4+CD25+ regulatory T cells in accordance with one embodiment of the present invention.

Methods: The steps of one embodiment of the method of generating and selecting antigen-specific CD4+CD25+ Treg cells are shown in FIG. 5. As shown, the method involves the steps of determining the MHC Class II status of the blood sample (100), isolating CD4+CD25− T cells from the sample (110), and inducing the CD4+CD25− T cells with antigen and antigen presenting cells to generate CD4+CD25+ regulatory T cells (120). The ex vivo generated antigen-specific CD4+ CD25+ T cells are stained with MHC Class II/cognate peptide (tetramer) complexes that are MHC Class II matched to the blood sample (130), and the CD4+CD25+Tmr+ population is sorted by FACS (140), and assayed for suppressor activity (150).

Isolation of Blood Samples: Blood samples were obtained from healthy volunteers participating in a research protocol approved by the institutional review board. The MHC Class II type of all participants was obtained by Dynal HLA Class II SSO typing kits (HLA-DRB SSO kit (product #810.45) and HLA-DQB1 SSO kit (product #820.01)), obtained from Dynal Biotech, LLC, Brown Deer, Wis.

Generation of Regulatory T cells: CD4+CD25− T cells were isolated from PBMC as described above in Example 1 from three DRB1 0401 positive subjects, previously vaccinated for flu. Purity was determined to be greater than 99% cells CD25− by FACS.

The CD4+CD25− cells ($3\times10^6$ cells/well in a 24 well plate) were cultured for 10 days in the presence of HA (306-319) 10 μg/ml and irradiated (5000 rads), CD4+ T cell depleted autologous APC (at $6\times10^6$ APC/well) in media containing RPMI plus 10% pooled human serum.

Isolation of Antigen-specific Regulatory T cells: After 10 days, HA antigen-specific CD4+CD25+Treg cells were stained with antibodies to CD4, CD25 and DR4 HA Tmr and FACS sorted into CD25+Tmr+, CD25+Tmr− and CD25− subgroups using DRB1 0401/HA (306-319) tetramers as described below:

1. Preparation of Soluble Tetrameric Class II MHC Peptide Complexes:

A. Construction of HLA-DR0401-leucine zipper-biotinylation site-expression vectors: The construction of the expression vectors for generation of the soluble DRA 0101/DRB1 0401 has been described previously in Novak et al., *J. Clin. Invest.* 104:R63-R67, 1999. Briefly, chimeric cassettes containing the coding regions for DR/leucine zipper (LZ) were made using the PCR-mediated splicing overlap technique (Horton et al., *Biotechniques* 8:528-535, 1990).

Soluble DRA1 Chain: To generate the soluble DRA1 chain, the cDNA of DRA1 0101 (GenBank No. M60334) was amplified using the primer pair DRA1 0101F and DRA1 0101R (sharing homology with the 5' end of basic leucine zipper as shown in TABLE 4). The first round PCR product was used as the initial forward primer on the pN15Lzalpha template, which contains the basic LZ motif, to form the DRA1/LZ chimera. The PCR primers DRA1-0101/LZ Chimera F and DRA1-0101/LZ Chimera R were then used to amplify the chimera. The resulting PCR product was TA cloned into the pCR2.1-TOPO vector (Invitrogen Corp, San Diego, Calif.), sequenced, and then subcloned into the Cu-inducible Drosophila expression vector pRM-HA-3 using the EcoR1 and Kpn1 restriction enzyme sites engineered into the second-round primers (underlined).

DRB1 soluble Chain: To generate the soluble DRB1 chain, cDNA of DRB1 0401 (Genbank No. L78166) was amplified in the first round using the primer pair DRB1-0401F and DRB1-0401R (sharing homology with the 5' end of acidic LZ). For the second round amplification, the first round product was used as initial forward primer on the pN15Lzbeta template containing the acidic LZ cDNA motif to form the DRB1/LZ chimera. The primer pair DRB-0401/LZ Chimera F and DRB-0401/LZ Chimera R were then used to amplify the chimera. The DRB1/LZ cassette was cloned in-frame 5' of the biotinylation sequence present in the vector pAC1 (Avidity, Denver, Colo.) using the Xho1 and HindIII restriction enzyme sites (underlined).

The complete DRB1/LZ/biotinylation site cassette was then amplified using the primer pair DRB-0401/LZ/BT F and DRB-0401/LZ/BT R. The fragment was TA cloned into pCR2.1-TOPO, sequenced, and then subcloned into the Drosophila expression vector pRm-Ha-3 using EcoR1 and Kpn1 sites (underlined).

2. Generation of DRA1 0101/DRB1 0401 Tetramers:

The chimeric cDNAs in the Schneider expression vectors pRmHa3 (carrying the soluble DRB1 chain and the soluble DRA1 chain) together with the plasmid pUChs-neo (which carries the neomycin resistance marker) were co-transfected into Schneider cells S-2 by standard calcium phosphate transfection techniques. Cells were selected with G418 at 2 mg/ml and expanded and grown to a density of $10^7$ cells/ml. $CuSO_4$ was added at a concentration of 1 mM to induce the production of soluble Class II molecules. The DR0401 molecules were purified by affinity chromatography using L243 as described by Stern et al., Cell 68:465-477, 1992.

The Class II molecules were concentrated to 2 mg/ml and then dialyzed against 10 mM Tris, pH 8.0, 10 mM NaCl. The protein was then biotinylated using the BirA enzyme according to the manufacturer's conditions (Avidity, Denver, Colo.). The excess biotin was removed by dialysis.

3. Peptide Loading:

The biotinylated DR0401 molecules were loaded with peptide by incubating for 72 hours at 37° C. with 10-fold molar excess of either hemagglutinin peptide residues HA(307-319), or tetanus toxoid peptide residues TT(830-843) in 100 mM $NaPO_4$, pH 5.5 and 0.2% n-octyl-D-glucopyranoside. Class II molecules were then incubated overnight at room temperature with phycoerythrin (PE)-streptavidin (BioSource International, Camarillo, Calif.) at an 8:1 molar ratio to allow the formation of tetrameric Class II peptide complexes.

Figure 7A:
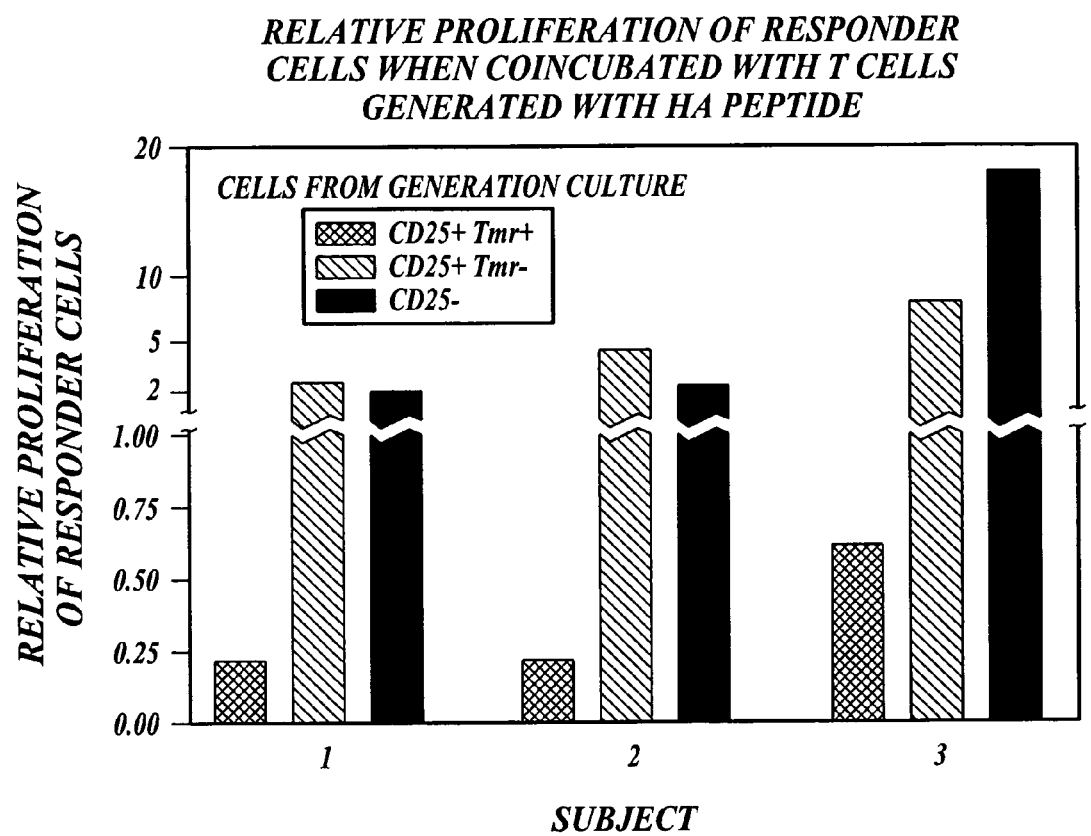
FIG. 7A presents graphical results demonstrating the relative proliferation of responder T cells when coincubated with ex vivo gene antigen-specific CD4+CD25+Tmr+ regulatory T cells generated with HA peptide, as described in Example 4.

Results: The results shown in FIG. 7A are presented as the mean of triplicates for three separate experiments and are representative of five separate experiments. The data was plotted relative to the proliferation observed in freshly isolated CD4+CD25− autologous responder cells, set at a value of 1. As shown, the CD25+HATmr+ population suppressed proliferation in response to HA(306-319). However, the CD4+CD25+HATmr− or CD4+CD25− cells did not show suppressor activity.

Cytokine Dependence: To test the dependence of the observed suppression on cytokines, 10 μg/ml anti-IL-10 (JES3-19F1, Pharmigen), anti-TGF-β1,2,3 (1D11 R&D Systems) or isotype matched controls (R35-95, MOPC-21, Pharmagen) were added to the proliferation assay described above.

Figure 7B:
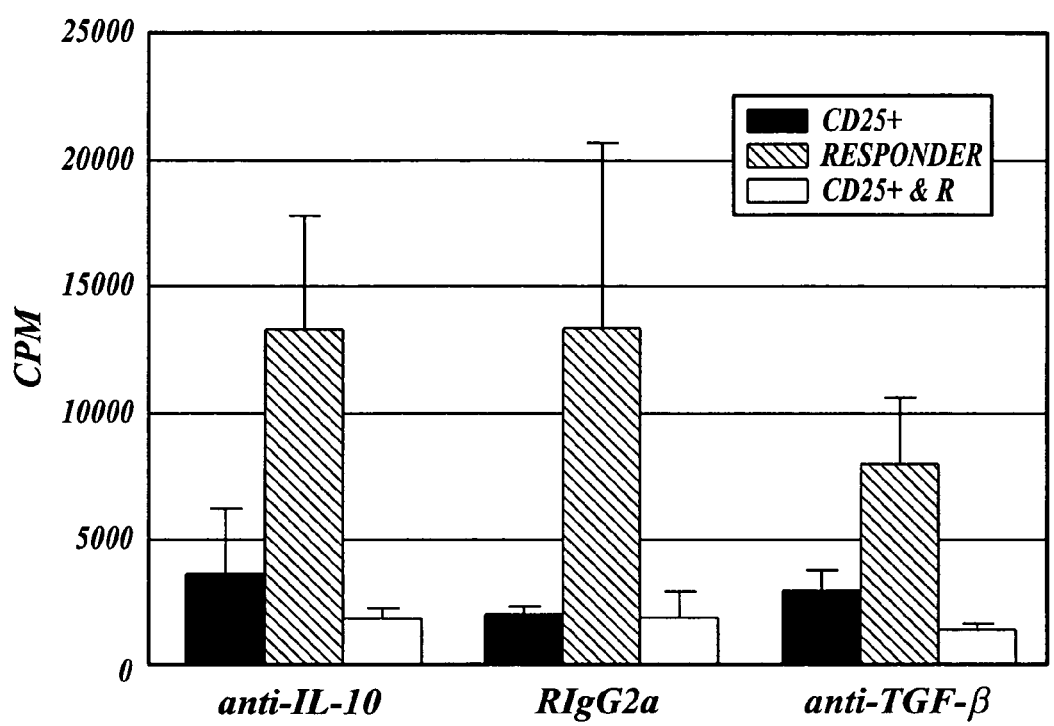
FIG. 7B presents graphical results demonstrating that the suppression demonstrated in FIG. 7A is cytokine independent, as described in Example 4.

Results: As shown in FIG. 7B, suppression was not inhibited by the blockade of IL-10 or TGF-β. This demonstrates that the ex vivo generated regulatory T cells are similar to freshly isolated CD4+CD25+ Treg from humans. It has pre-

TABLE 4

PCR PRIMERS USED TO FORM TETRAMER CONSTRUCTS

| NAME | SEQUENCE | TEMPLATE |
|---|---|---|
| DRA1-0101 F | 5'AGAATTCATGGCCATAAGTGGAGTCCC 3' (SEQ ID NO:56) | DRA1 0101 cDNA |
| DRA1-0101R | 5'CCAGGTCTGCTGACGACTCTGTAGTCTCTGGG 3' (SEQ ID NO:57) | DRA1 0101 cDNA |
| DRA1-0101/ LZ Chimera F | 5'AGAATTCATGGCCATAAGTGGAGTCCC3' (SEQ ID NO:58) | DRA1-0101/LZ Chimera |
| DRA1-0101/ LZ Chimera R | 5'CTGGTACCATCCTACTGGGCGAGTT3' (SEQ ID NO: 59) | DRA1-0101/LZ Chimera |
| DRB1-0401F | 5'ACTCGAGCCATGGTGTGTCTGAAGTTCCC3' (SEQ ID NO: 60) | DRB1 0401 cDNA |
| DRB1-0401R | 5'CCAGGTCTGCTGACGACTTGCTCTGT3' (SEQ ID NO: 61) | DRB1 0401 cDNA |
| DRB-0401/LZ Chimera F | 5'ACTCGAGCCATGGTGTGTCTGAAGTTCCC3' (SEQ ID NO: 62) | DRB1 0401/LZ chimera |
| DRB-0401/LZ chimera R | 5'ACAAGCTTGCCTGAGCCAGTTCCTTTTCC3' (SEQ ID NO: 63) | DRB1 0401/LZ chimera |
| DRB-0401/ LZ/BT F | 5'AGAATTCATGGTGTGTCTGAAGTTCCC3' (SEQ ID NO: 64) | DRB-0401/LZ/BT |
| DRB-0401/ LZ/BT R | 5'CT+ee,uns GGTACC+ee TTAGTGCCATTCGATTTTCTG3' (SEQ ID NO: 65) | DRB-0401/LZ/BT |

4. Selection with DRB 0401/HA(306-319) Tetramers:

After 10 days in culture, the culture was incubated for 1 hour at 37° C. with 50 μg/ml DRB 0401/HA(306-319) Tmr and sorted by FACS. The resulting populations were approximately 18% CD4+CD25+Tmr+; 13% CD4+CD25+Tmr− and 68% CD4+CD25−.

Proliferation Assays: The three sorted cell populations were tested for their ability to suppress proliferation of freshly isolated, autologous CD4+CD25− T responder cells in response to HA(306-319). Each group of sorted cells was added at a ratio of 1:1 (25,000 CD25+Tmr+cells/well) to a culture of freshly isolated autologous CD4+CD25− with irradiated APC (100,000 APC/well) and 10 μg/ml HA (307-319) peptide in media containing RPMI plus 10% pooled human serum.

viously been shown that the addition of 10 μg/ml of anti-IL-10 or anti-TGF-β ablates the suppressive activity of T regulatory type 1 (TR1) cells in humans (Jonuleit et al., J. Exp. Med. 196:255-260, 2002; Dieckmann et al., J. Exp. Med 196:247-253, 2002).

Figure 7C:
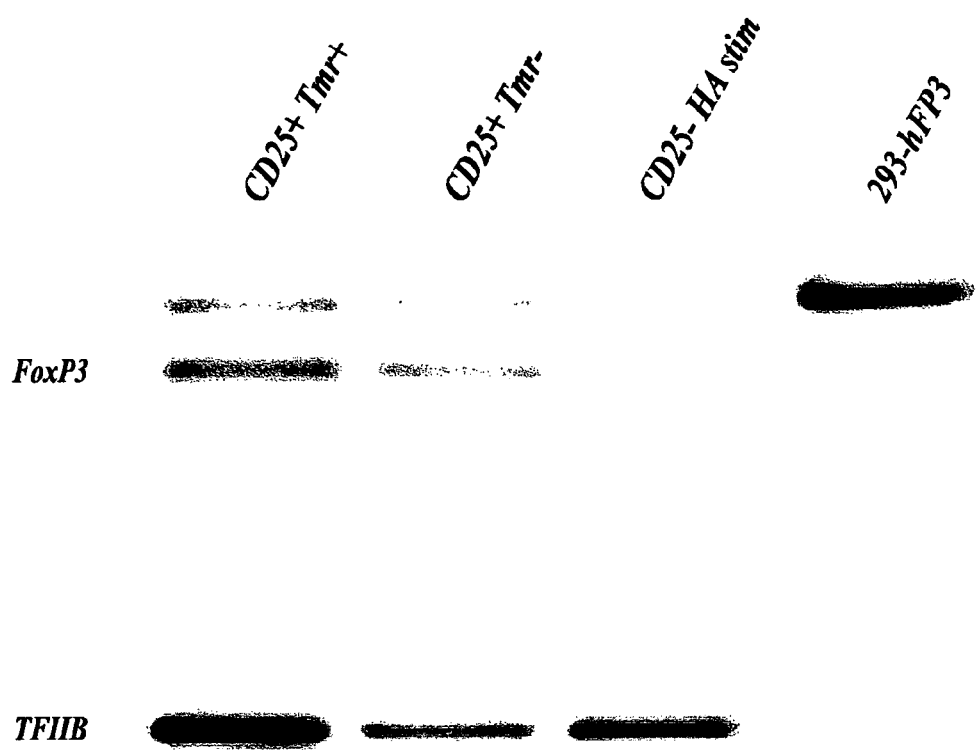
FIG. 7C presents Western blot data demonstrating that FoxP3 protein expression is observed in both antigen-specific CD25+Tmr+ regulatory T cells and non specific CD25+Tmr− regulatory T cell populations, as described in Example 4.

Western Blot Analysis: As shown in FIG. 7C, FoxP3 protein expression correlates with CD25+ expression and is present in both CD25+Tmr+ and CD25+Tmr− cell populations.

Discussion: These results demonstrate that antigen-specific Treg can be generated with induction to a foreign antigen. The resulting Treg cells suppress responder cell proliferation upon re-activation by the cognate antigen. In contrast, suppression was not seen with the CD25+Tmr− or CD25− T cells derived from the same induction culture. It is important to note that not all cells present in the generation system become regulatory. Only those T cells that remain CD25+10 days post activation and are FoxP3+ have suppressive function. In typical induction cultures, the majority of T cells present after 10 days have become CD25−. Therefore, the ex vivo generated CD4+CD25+ Treg population is a dedicated lineage of regulatory cells persisting within the T cell response. It is also important to note that traditional re-stimulation of human T cell lines and clones is done with the addition of exogenous IL-2. The in vitro proliferation assay, however, measures proliferation of responder T cells in the absence of IL-2. In fact, suppression is abrogated in the presence of IL-2. Therefore, the presence and/or activity of CD4+ CD25+Treg cells is unlikely to be observed under the standard culture conditions used to grow antigen-specific T cells.

EXAMPLE 5

This example demonstrates that antigen-specific CD4+ CD25+Tmr+ Treg cells require re-exposure to the cognate antigen in order to have suppressor function. However, once activated, the Treg cells suppress T responder cells in response to both cognate and noncognate antigens.

Methods and Materials: CD4+CD25+HATmr+ and CD4+ CD25−HATmr− were generated as described above in Example 4.

Proliferation Assay: Antigen-specific Treg cells generated by induction with HA were sorted and tested for their ability to suppress T responder proliferation in response to a tetanus antigen. CD25+Tmr+ and CD25−Tmr− were cultured with freshly isolated CD25− cells from the same donor at a 1:1 ratio and stimulated with either 10 μg/ml HA (306-319) and/ or 10 μg/ml Tetanus toxoid. The ability of CD4+CD25+ Treg cells to suppress the proliferation of freshly isolated CD4+ CD25− responder T cells in response to various antigens was determined by adding $^3$H thymidine during the final 16 hours of a 6-7 day assay and proliferation was measured by scintillation counting.

Figure 8A:
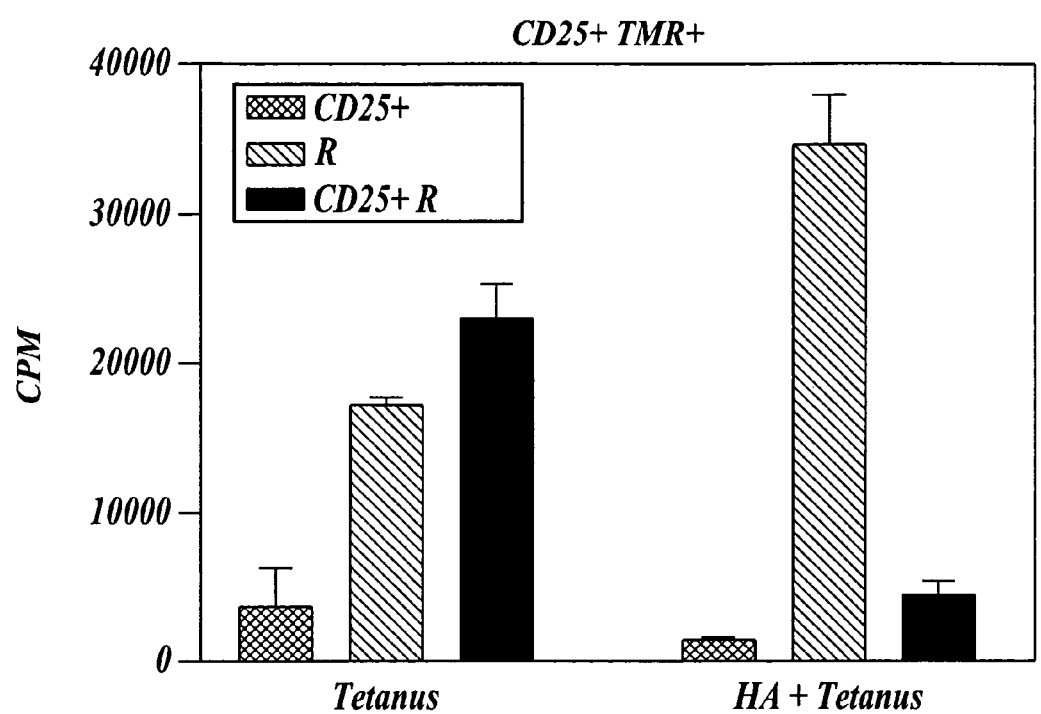
FIG. 8A presents results demonstrating that a sorted population of CD25+Tmr+ antigen-specific regulatory T cells derived from an induction culture with an HA peptide require cognate antigen (HA) stimulation in order to suppress CD4+CD25− responder T cells, however, once activated, the CD25+Tmr+ regulatory T cells demonstrate bystander suppression and suppress responder cell proliferation to cognate antigen (HA) and an unrelated antigen (tetanus), as described in Example 5.

Results:

FIG. 8A shows the results of the proliferation assay testing CD4+CD25+Tmr+ cells exposed to tetanus or re-exposed to HA plus tetanus antigen. As shown, the HA derived CD25+ Tmr+ cells were anergic alone, and were not able to suppress responder cell proliferation after exposure to tetanus peptide. In contrast, when the same Treg population was re-exposed to HA plus tetanus peptide, the activated Treg cells suppressed the responder T cells in response to both HA and Tetanus, demonstrating that, once activated, the antigen-specific Treg cells are capable of non-specific bystander suppression to noncognate antigens.

Figure 8B:
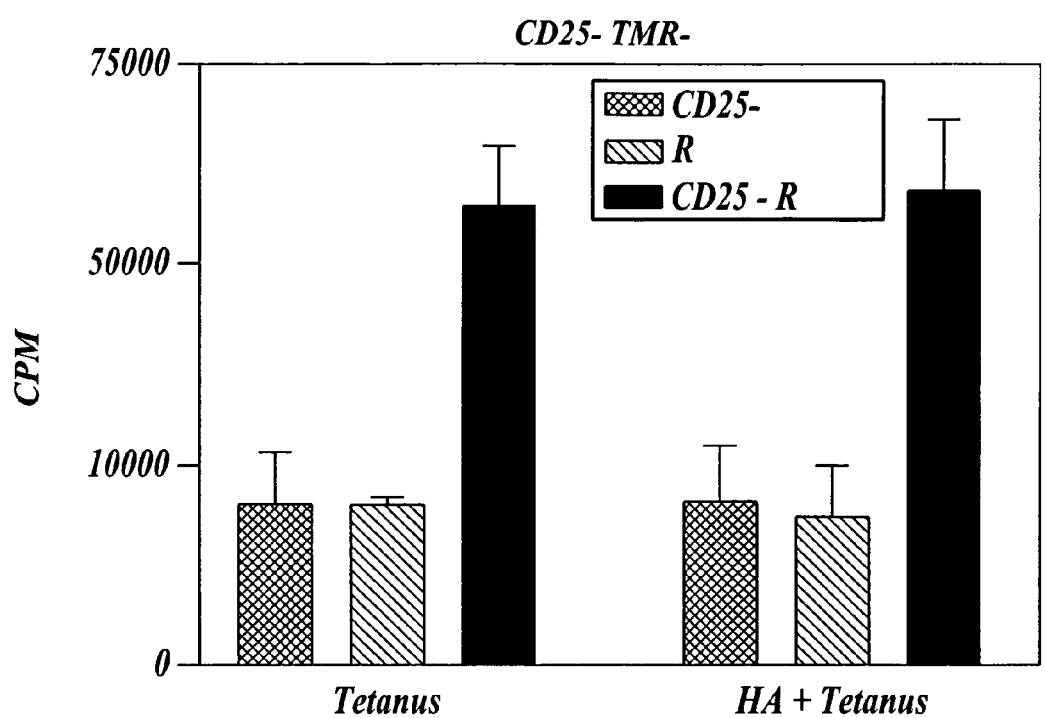
FIG. 8B presents results demonstrating that a sorted population of CD25−Tmr− cells derived from an induction culture with an HA peptide do not suppress the proliferation of freshly isolated CD4+CD25− responder cells in the presence of cognate antigen (HA) or an unrelated antigen (tetanus), as described in Example 5.
Figure 8C:
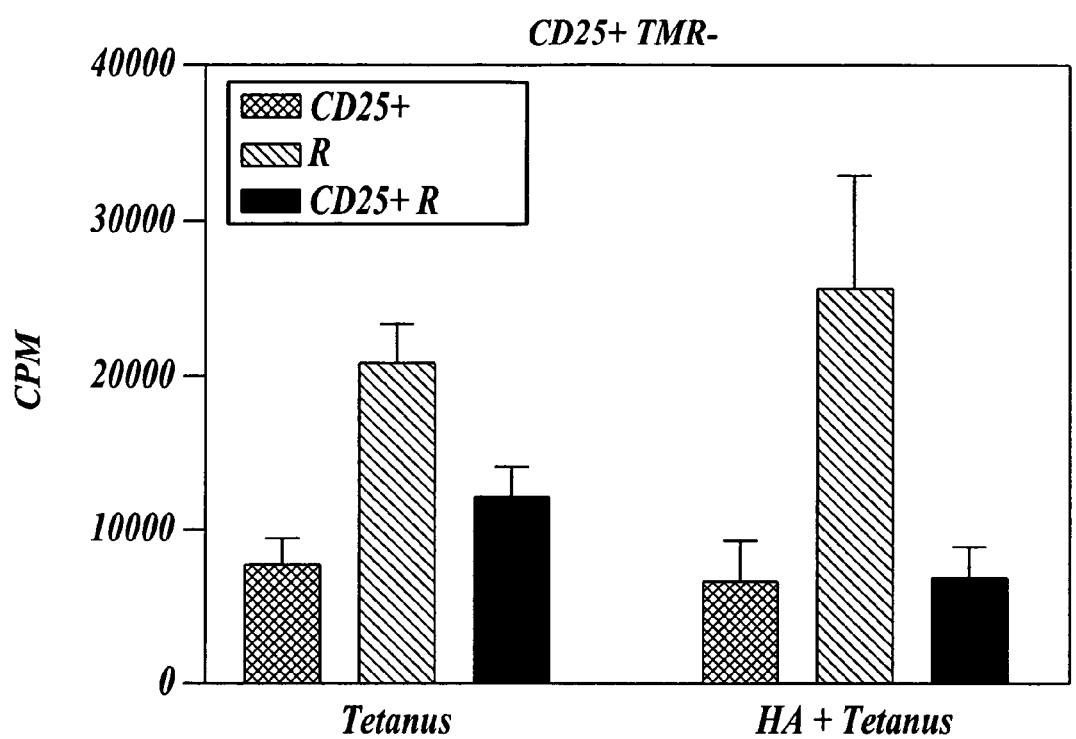
FIG. 8C presents results demonstrating that a sorted population of CD25+Tmr− cells derived from an induction culture with an HA peptide suppress the proliferation of freshly isolated CD4+CD25− responder cells in a non-specific manner, in the presence of either the cognate antigen (HA) or an unrelated antigen (tetanus), as described in Example 5.

FIG. 8B shows the results of the proliferation assay testing CD4+CD25−Tmr− cells exposed to tetanus or re-exposed to HA plus tetanus antigen. As shown in FIG. 8B, the CD25− cells do not suppress responder T cell proliferation in response to tetanus or HA antigen.

FIG. 8C shows the results of the proliferation assay testing CD4+CD25+Tmr− cells. As shown, the CD25+Tmr− cells induced in the presence of HA antigen do function to suppress responder T cells, however, this population of regulatory cells is activated in the presence of either tetanus or HA antigen. Therefore, the Tmr− regulatory cells are non-specifically activated in the absence of re-exposure of cognate antigen.

Discussion: While not wishing to be bound by theory, these data suggest a model whereby antigen-specific Treg cells are generated during an immune response in humans and are involved in controlling the spread of the response. The Treg cells may be generated either following activation of naïve cells, or from effector cells later in the response. These Treg cells are then responsible for controlling the spread of the response through suppression of both responder effector cells as well as bystander activated cells. In this way, the antigen-specific Treg cells only become activated in an antigen-specific manner upon re-exposure to cognate antigen at the site of inflammation and, once activated, would be capable of suppressing bystander cells in a cell-cell contact dependent manner.

EXAMPLE 6

This example describes the generation of GAD65 antigen-specific regulatory T cells from CD4+CD25− cells isolated from diabetic patients.

Methods and Materials:

Individuals with newly diagnosed T1DM were HLA typed, and HLA Class II matched controls were recruited for this study. 200 cc of blood was obtained from each donor. CD4+ CD25− T cells and autologous antigen presenting cells were obtained as described above in Example 1.

Generation of CD4+CD25+Treg cells: Was achieved by incubating the CD4+CD25− T cells for 10 days with CD4+ depleted APC derived from the subjects and 10 μg/ml GAD65 (555-567) peptide.

Selection of Antigen-specific Treg Cells: After 10 days in culture, the cells in the induction culture were stained with antibodies to CD4, CD25 and DR4 GAD65 Tmr and FACS sorted into CD25+Tmr+, CD25+Tmr−, and CD25− subgroups.

Figure 9A:
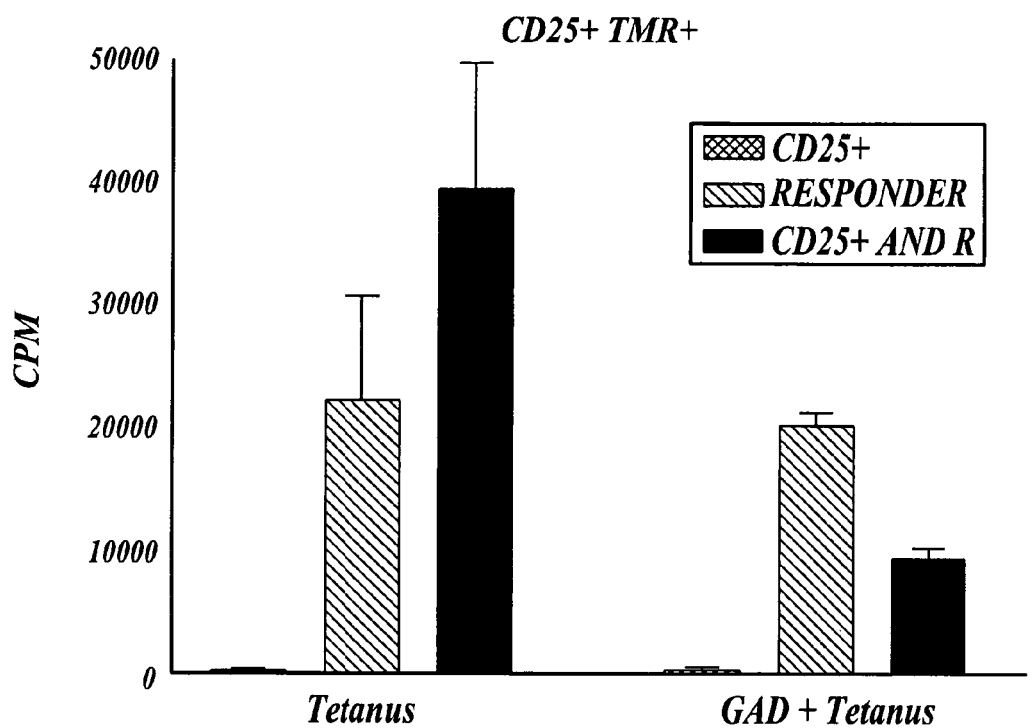
FIG. 9A presents results demonstrating that a sorted population of CD25+Tmr+ cells derived from an induction culture with a GAD peptide require cognate antigen (GAD) stimulation in order to suppress CD4+CD25− responder t cells, however, once activated, the CD25+Tmr+ regulatory T cells demonstrate bystander suppression and suppress responder cell proliferation to cognate antigen (GAD) and an unrelated antigen (tetanus), as described in Example 6.

Results: FIG. 9A shows the results of the proliferation assay testing CD4+CD25+Tmr+ cells activated with tetanus or GAD plus tetanus antigen. As shown in FIG. 9A, the GAD induced CD25+Tmr+cells were anergic alone, and were not able to suppress responder cell proliferation after exposure to tetanus peptide. When the same population was re-exposed to GAD65 peptide plus tetanus peptide, the activated Treg cells did suppress the responder T cells in response to both GAD65 and Tetanus peptides, again demonstrating that, once activated, the antigen-specific Treg cells are capable of non-specific bystander suppression.

Figure 9B:
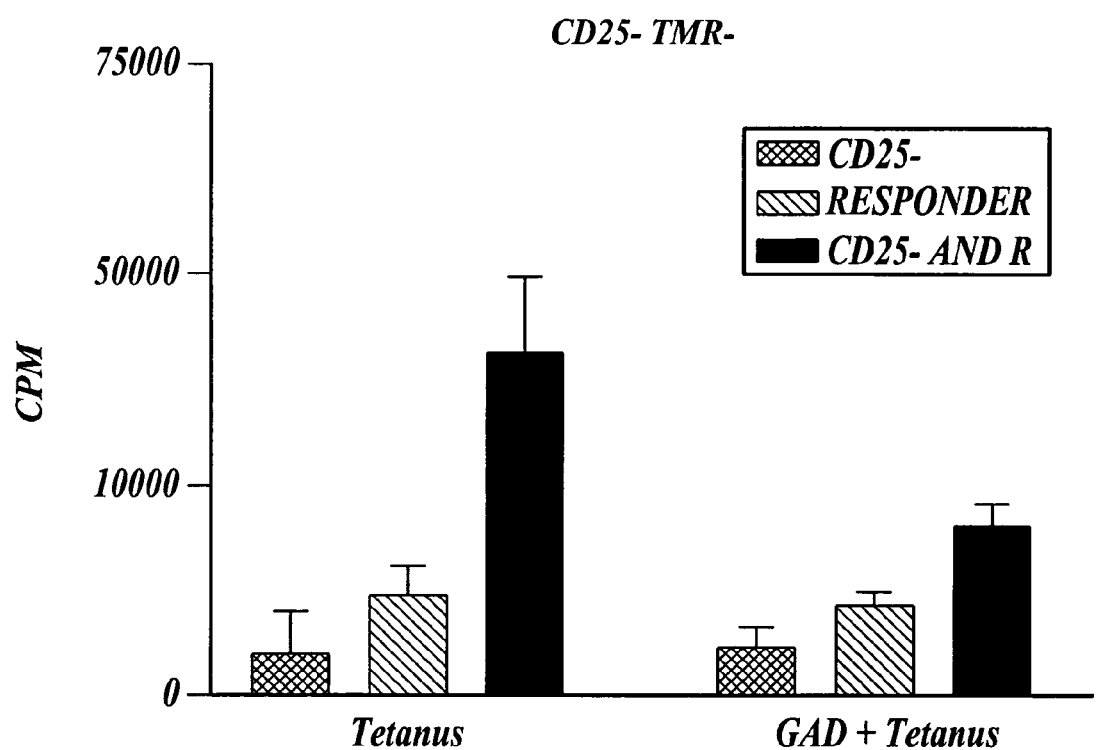
FIG. 9B presents results demonstrating that a sorted population of CD25−Tmr− cells derived from an induction culture with a GAD peptide do not suppress the proliferation of freshly isolated CD4+CD25− responder cells in the presence of cognate antigen (GAD) or an unrelated antigen (tetanus), as described in Example 6.

FIG. 9B shows the results of the proliferation assay testing CD4+CD25−Tmr− cells activated with tetanus or GAD65 plus tetanus antigen. As shown in FIG. 9B, the CD25− cells do not suppress responder T cell proliferation in response to tetanus or GAD65 antigen.

Discussion: This data demonstrates that the generation of GAD65 specific Treg cells is possible in CD4+CD25− cells derived from a diabetic patient in contrast to early reports that individuals with T1DM have few or poorly functional Treg in vivo (see Krigel et al., *J. Exp. Med.* 199:1285-1291, 2004; Kukreja et al., *J. Clin. Invest.* 109:131-140, 2002). More recent reports have contradicted those findings and demonstrate that diabetic subjects have functional T regulatory cells (Putnam et al., *J. Autoimmun.* 24:55-62, 2005). The ex vivo generated GAD specific Treg cells may be used to treat subjects at risk or suffering from type 1 diabetes according to the methods described herein.

EXAMPLE 7

Figure 10A:
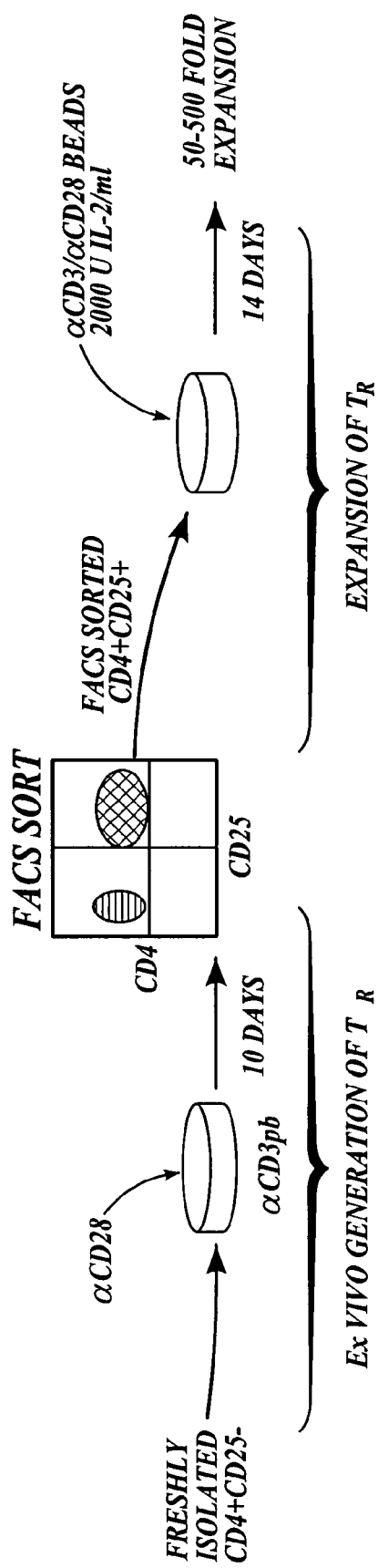
FIG. 10A is a schematic diagram illustrating a method of generating CD4+CD25+ regulatory T cells in an ex vivo culture system from CD4+CD25− cells with anti-CD3 and anti-CD28 induction agents and expanding the CD4+CD25+ regulatory T cell population, as described in Example 7.

This example describes a method of expanding a population of ex vivo generated regulatory T cells using antiCD3/ CD28 beads as illustrated in FIG. 10A.

Methods:

Generation of Treg cells: Treg cells were generated with plate-bound anti-CD3 and soluble anti-CD28 overnight under the conditions described in Example 1. After the overnight culture, the cells were transferred to a new well and cultured for 9 additional days and FACS sorted based on CD25+ expression.

Expansion of Treg Cells: CD4+CD25+ Treg cells were expanded 50-500 fold by culturing at a 1:1 ratio with anti-CD3/anti-CD28 beads (Xcyte Therapeutics, Inc.) plus rhIL-2 (2000 U/ml) (Chiron Corp.) for 14 days in complete medium (10% heat-inactivated human serum, nonessential amino acids, 0.5 mM sodium pyruvate, 5 mM Hepes, 1 mM glutaMax and 55 µM β-mercaptoethanol in complete RPMI plus penicillin and streptomycin).

Analysis of Expanded Tregs: At the end of the culture period, the anti-CD3 and anti-CD28 beads were removed using AutoMACS. The cells were sorted into CD4+CD25+ and CD4+CD25– populations and assayed for FoxP3 expression by Western blot as described in Example 1. To test the suppression, CD4+CD25+ cells and CD4+CD25– cells from the expansion culture were cultured either alone or in combination at a 1:1 ratio with freshly isolated CD4+CD25– responder T cells from the same donor. The cells were activated with anti-CD3/anti-CD28 as previously described in Example 1. Proliferation was measured after six days by $^3$H-thymidine incorporation.

Figure 10B:
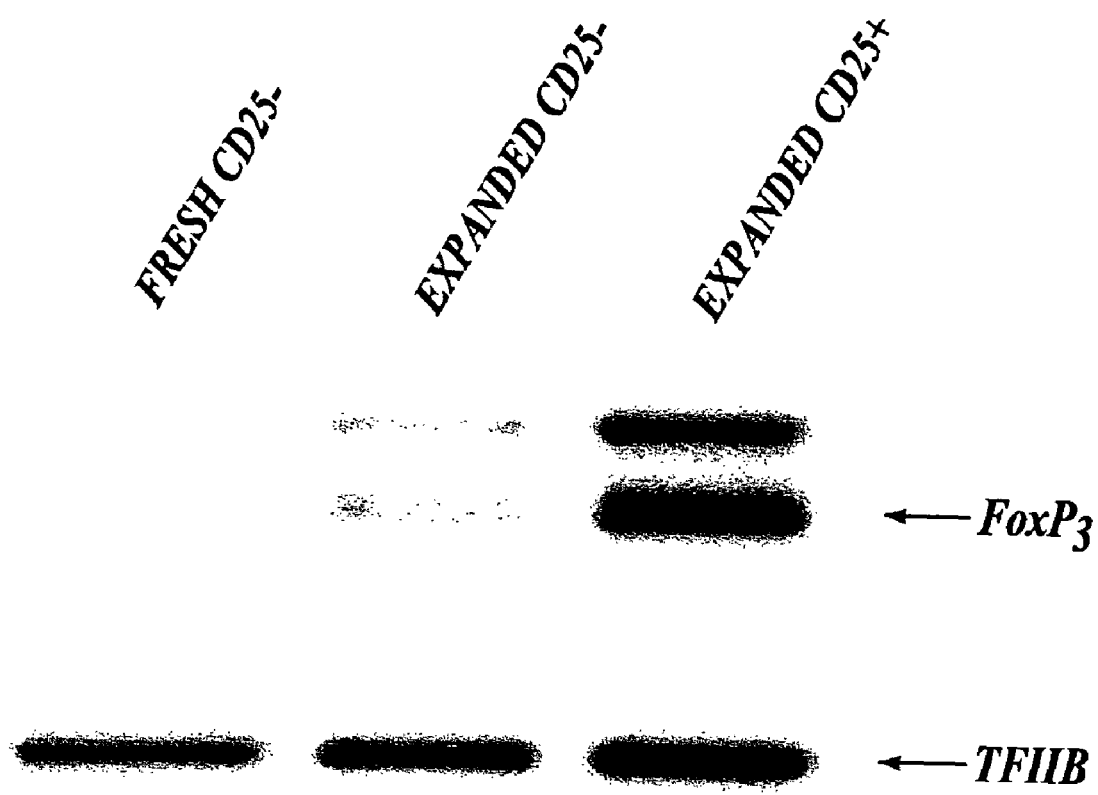
FIG. 10B shows Western blot data demonstrating that FoxP3 is expressed in both the CD25− and CD25+ populations of the expanded, ex vivo generated regulatory T cell population, as described in Example 7.
Figure 10C:
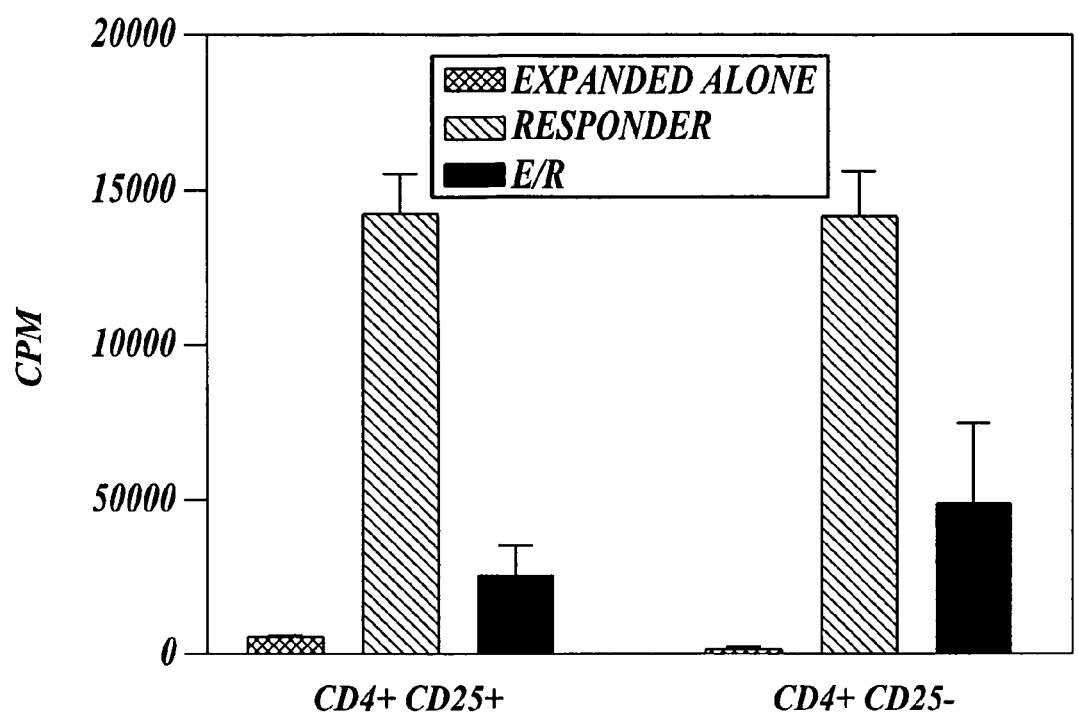
FIG. 10C presents graphical results demonstrating that ex vivo generated and expanded CD4+CD25+ regulatory T cells induced with plate-bound anti-CD3 and soluble anti-CD28 suppress the proliferation of freshly isolated CD4+CD25− responder T cells, as described in Example 7.

Results: The results of the Western blot analysis of expanded Treg cells is shown in FIG. 10B. The results of the proliferation assay using the expanded cell populations is shown in FIG. 10C. As shown, the expanded CD4+CD25+ Treg cells continue to express FoxP3 protein at a high level. In addition, a lower level of FoxP3 expression is detected in the expanded CD4+CD25– cells. This demonstrates that FoxP3 expression persists in all of the cells in culture, even when CD25 is not present. This result, combined with the ability of the CD4+CD25– cells to suppress proliferation demonstrates that we have expanded a group of cells which retain regulatory function in response to anti-CD3/anti-CD28.

The expansion method described may also be used to expand antigen-specific Treg cells by generating antigen-specific CD4+CD25+ Treg as described above in Examples 5 and 6, selecting for CD4+CD25+Tmr+ cells, and culturing the selected cells in RPMI media containing 2000 U/ml IL-2 for 10-14 days. Expansion of the Treg cells may be further optimized by adding anti-CD3/anti-CD28 Xcyte beads at a bead-to-cell ratio ranging from a 1:1 ratio to a 1:10 ratio to the expansion culture. Plate-bound MHC Class II monomers specific to the antigen may also be added with or without the anti-CD3/anti-CD28 Xcyte beads. At the end of the culture period, the antigen-specific Treg cells may be repurified from the expansion culture using the CD4+CD25+Tmr+ selection as described above in Examples 5 and 6.

While the preferred embodiment of the invention has been illustrated and described, it will be appreciated that various changes can be made therein without departing from the spirit and scope of the invention.

The embodiments of the invention in which an exclusive property or priviledge is claimed are defined as follows:

1. A method for generating a T cell population comprising human antigen-specific CD4+CD25+regulatory T cells from freshly isolated CD4+CD25– T cells, the method comprising:
   (a) isolating CD4+CD25– T cells from a sample comprising T cells obtained from a human subject;
   (b) determining the MHC Class II type of the subject;
   (c) inducing generation of antigen-specific regulatory T cells by contacting the isolated CD4+CD25– T cells in a culture vessel with a CD4+CD25+induction agent comprising one or more antigenic peptide(s) and a population of MHC expressing antigen presenting cells that are MHC class II matched to the subject, for a time period sufficient to generate antigen-specific CD4+CD25+ regulatory T cells;
   (d) selecting the CD4+CD25+antigen-specific regulatory T cells by sorting the cells in the induction culture with a selection agent comprising at least one artificial multimeric MHC Class II/peptide complex, wherein the MHC Class II/peptide complex is chosen to correspond to the MHC Class II type of the subject;
   (e) isolating the subpopulation of cells selected from the induction culture of step (d) that express CD25+, wherein at least 70% of the subpopulation of cells isolated from the induction culture bind to the corresponding MHC Class II/peptide tetramer complex and are CD4+CD25+antigen-specific regulatory T cells; and
   (f) assaying at least a portion of cells isolated according to step (e) for FoxP3 expression, wherein the CD4+CD25+ antigen specific regulatory T cells express FoxP3.

2. The method according to claim 1, further comprising expanding the CD4+CD25+antigen-specific regulatory T cell population.

3. The method of claim 2, further comprising assaying the expanded CD4+CD25+antigen-specific regulatory T cell population for FoxP3 expression.

4. The method according to claim 1, wherein the antigen presenting cells are autologous to the subject.

5. The method according to claim 1, wherein the antigen presenting cells are heterologous to the subject.

6. The method according to claim 1, wherein the antigenic peptide is derived from a self-antigen.

7. The method according to claim 6, wherein the self-antigen is associated with an autoimmune disease.

8. The method according to claim 7, wherein the autoimmune disease is selected from the group consisting of: type 1 diabetes, multiple sclerosis, rheumatoid arthritis, psoriatic arthritis, autoimmune myocarditis, pemphigus, celiac disease, myasthenia gravis, Hashimoto's thyroiditis, Graves' disease, Addison's disease, autoimmune hepatitis, autoimmune hypothyroidism, chronic beryllium syndrome, chronic lyme arthritis, familial dilated cardiomyopathy, Goodpasture's syndrome, insulin autoimmune syndrome, juvenile dermatomyositis, polychondritis, scleroderma, and Sjogren's syndrome.

9. The method according to claim 8, wherein the antigenic peptide is derived from a self-antigen associated with type 1 diabetes.

10. The method according to claim 9, wherein the self-antigen is an islet protein.

11. The method according to claim 10, wherein the islet protein is glutamic acid decarboxylase (GAD65).

12. The method according to claim 11, wherein the antigenic peptide is GAD65 555-567 (SEQ ID NO: 4).

13. The method according to claim 1, wherein the antigenic peptide is derived from a foreign antigen.

14. The method of claim 1, wherein the isolated CD4+ CD25– T cells of step (a) comprise at least 95% CD4+CD25– cells.

15. The method of claim 1, wherein the method further comprises enriching the isolated CD4+CD25– T cells of step (a) for memory T cells prior to step (b).

16. The method of claim 1, wherein at least 80% of the subpopulation of cells isolated from the induction culture bind to the corresponding MHC ClassII peptide tetramer complex and are CD4+CD25+.

17. The method of claim 1, wherein isolating the subpopulation of cells selected from the induction culture according to step (e) comprises contacting the induction culture of step (d) with an anti-CD25 antibody.

18. The method of claim 1, wherein the isolated CD4+ CD25– T cells of step (a) comprise at least 99% CD4+CD25– cells.

19. The method of claim 1, further comprising assaying at least a portion of the cells isolated according to step (e) for the ability to suppress the proliferation of CD4+CD25– responder T cells after re-exposure to the cognate antigen.

* * * * *